(12) United States Patent
Nakamura

(10) Patent No.: US 10,898,612 B2
(45) Date of Patent: Jan. 26, 2021

(54) CELL STRUCTURE AND METHOD FOR PRODUCING CELL STRUCTURE

(71) Applicant: FUJIFILM Corporation, Tokyo (JP)

(72) Inventor: Kentaro Nakamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/866,735

(22) Filed: Jan. 10, 2018

(65) Prior Publication Data

US 2018/0140745 A1    May 24, 2018

Related U.S. Application Data

(63) Continuation of application No. PCT/JP2016/070211, filed on Jul. 8, 2016.

(30) Foreign Application Priority Data

Jul. 10, 2015 (JP) .................. 2015-138546

(51) Int. Cl.

| | |
|---|---|
| *A61L 27/38* | (2006.01) |
| *A61K 35/34* | (2015.01) |
| *A61K 35/44* | (2015.01) |
| *A61L 27/00* | (2006.01) |
| *A61K 35/407* | (2015.01) |
| *A61K 35/28* | (2015.01) |
| *A61K 35/33* | (2015.01) |
| *A61L 27/22* | (2006.01) |

(52) U.S. Cl.
CPC .......... *A61L 27/3886* (2013.01); *A61K 35/28* (2013.01); *A61K 35/33* (2013.01); *A61K 35/34* (2013.01); *A61K 35/407* (2013.01); *A61K 35/44* (2013.01); *A61L 27/00* (2013.01); *A61L 27/222* (2013.01)

(58) Field of Classification Search
None
See application file for complete search history.

(56) References Cited

U.S. PATENT DOCUMENTS

| | | | | |
|---|---|---|---|---|
| 6,992,172 | B1 * | 1/2006 | Chang ................ | A61K 8/65 435/320.1 |
| 2007/0160543 | A1 * | 7/2007 | Moller .................. | A61J 1/067 424/46 |
| 2012/0329157 | A1 | 12/2012 | Nakamura | |
| 2013/0004549 | A1 * | 1/2013 | Nakamura ............ | A61L 27/18 424/400 |
| 2013/0071441 | A1 | 3/2013 | Iwazawa et al. | |
| 2014/0099709 | A1 | 4/2014 | Presnell et al. | |
| 2014/0341862 | A1 | 11/2014 | Haverich et al. | |
| 2015/0352252 | A1 | 12/2015 | Nakamura et al. | |
| 2016/0177270 | A1 | 6/2016 | Takebe et al. | |
| 2017/0274021 | A1 | 9/2017 | Haverich et al. | |

FOREIGN PATENT DOCUMENTS

| | | |
|---|---|---|
| CN | 1895684 A | 1/2007 |
| CN | 1921896 A | 2/2007 |
| CN | 102858381 A | 1/2013 |
| CN | 104717987 A | 6/2015 |
| DE | 10 2011 112955 A1 | 3/2013 |
| EP | 3050580 A1 | 8/2016 |
| JP | 5-168470 A | 7/1993 |
| JP | 2009-112233 A | 5/2009 |
| JP | 2014-012114 A | 1/2014 |
| WO | 2011/108517 A1 | 9/2011 |
| WO | 2014/133081 A1 | 9/2014 |
| WO | 2015/012158 A1 | 1/2015 |
| WO | 2015/046216 A1 | 4/2015 |

OTHER PUBLICATIONS

Extended European Search Report (EESR) dated Jun. 4, 2018, from the European Patent Office in counterpart European Application No. 16824394.7.
International Search Report dated Sep. 6, 2016, in counterpart International Application No. PCT/JP2016/070211.
Written Opinion of the International Searching Authority dated Sep. 6, 2016, in counterpart International Application No. PCT/JP2016/070211.
International Preliminary Report on Patentability dated Jan. 16, 2018, in counterpart International Application No. PCT/JP2016/070211.
Office Action dated Aug. 14, 2018 from the Japanese Patent Office in counterpart JP Application No. 2017-528652.
Office Action dated Mar. 17, 2020, from the China National Intellectual Property Administration in CN Application No. 201680040735.4.

(Continued)

*Primary Examiner* — Thomas J. Visone
(74) *Attorney, Agent, or Firm* — Sughrue Mion, PLLC

(57) ABSTRACT

An object of the present invention is to provide a cell structure which can be produced within a short period of time and has a predetermined or larger size, and a method for producing the above-described cell structure. According to the present invention, there is provided a cell structure including: a biocompatible macromolecular block; and two or more kinds of cells, in which a plurality of the biocompatible macromolecular blocks are arranged in gaps between a plurality of the cells, and in which the two or more kinds of cells contain at least one kind of first cell selected from the group consisting of vascular endothelial cells, cardiac muscle cells, pancreatic islet cells, liver cells, epithelial cells, endothelial cells, nerve cells, embryonic stem cells, induced pluripotent stem cells, corneal epithelial cells, and retinal pigment epithelial cells, and at least one kind of second cell selected from the group consisting of mesenchymal cells, stromal cells, fibroblasts, smooth muscle cells, myoblasts, mesenchymal stem cells, adipose-derived stem cells, and umbilical cord-derived stem cells.

12 Claims, 8 Drawing Sheets

Specification includes a Sequence Listing.

(56) References Cited

OTHER PUBLICATIONS

Notice of Reasons for Revocation dated Sep. 13, 2019, from the Japanese Patent Office in counterpart Japanese application No. 2019-700446.
Office Action dated Sep. 25, 2020 from the China National Intellectual Property Administration in Chinese Application No. 201680040735.4.
Communication in European Application No. 16 824 394.7 dated Dec. 4, 2020, 4 pages.

* cited by examiner

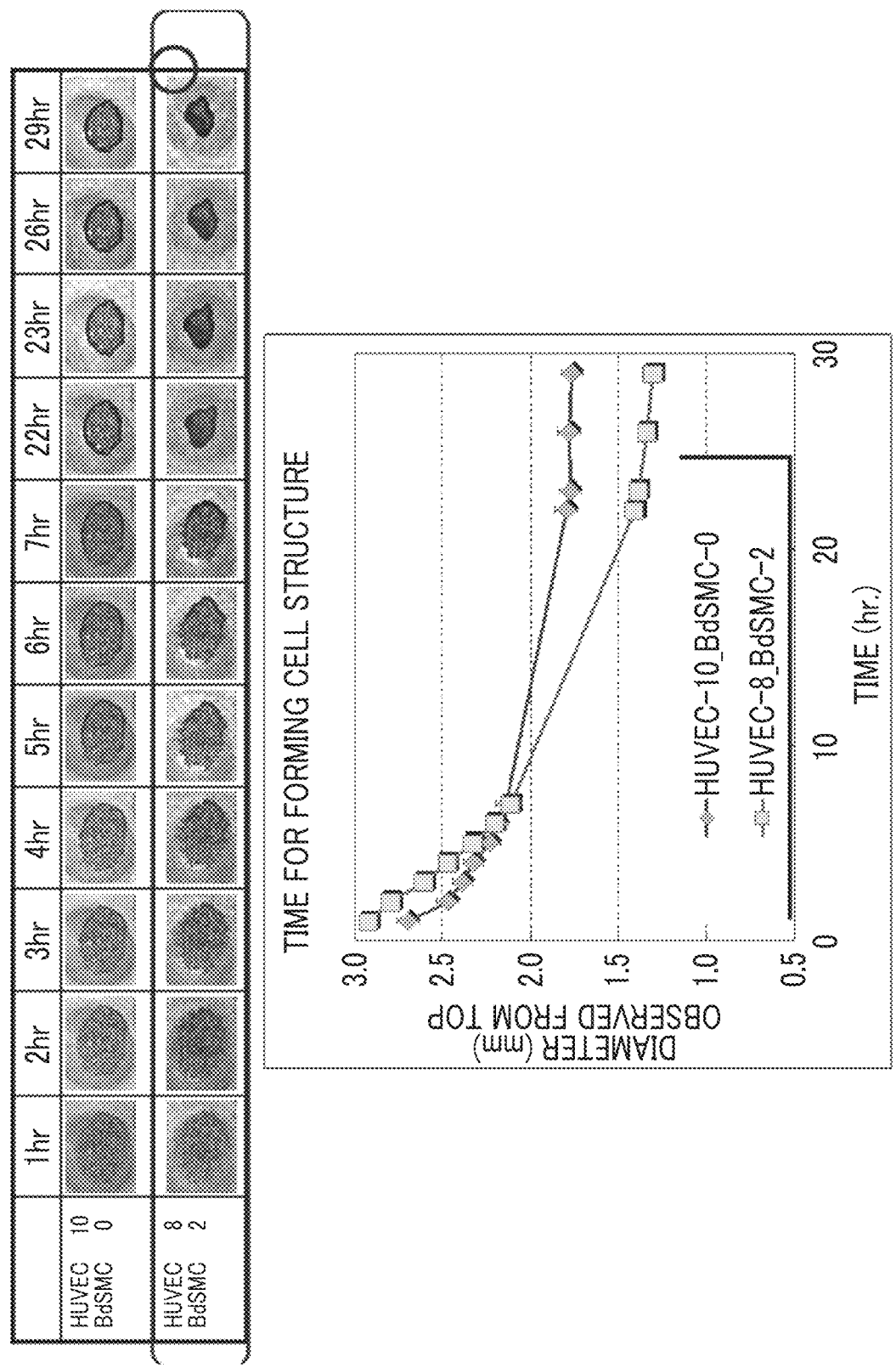

CELL STRUCTURE AND METHOD FOR PRODUCING CELL STRUCTURE

CROSS-REFERENCE TO RELATED APPLICATIONS

This application is a Continuation of PCT International Application No. PCT/JP2016/070211 filed on Jul. 8, 2016, which claims priority under 35 U.S.C § 119(a) to Japanese Patent Application No. 2015-138546 filed on Jul. 10, 2015. Each of the above application(s) is hereby expressly incorporated by reference, in its entirety, into the present application.

BACKGROUND OF THE INVENTION

1. Field of the Invention

The present invention relates to a cell structure and a method for producing the cell structure.

2. Description of the Related Art

Currently, regenerative medicine, which regenerates living body tissues and organs having functional disorders or dysfunction, is put into practical use. The regenerative medicine is new medical technology creating a form or a function of a living body tissue that cannot be recovered with only natural healing ability possessed by a living body, which is the same as that of an original tissue, again, using three factors including a cell, a scaffold, and a growth factor. In recent years, treatment using cells is gradually realized. Examples thereof include cartilage treatment using autologous chondrocytes, and cultured epidermis using autologous cells; bone regeneration treatment using mesenchymal stem cells; myocardial cell sheet treatment using myoblasts; cornea regeneration treatment using corneal epithelial sheets; and nerve regeneration treatment. These kinds of new treatment achieve restore and regenerate a living body tissue unlike alternative medicine using artificial substances (for example, an artificial bone prosthetic material or hyaluronic acid injection), and can achieve a high therapeutic effect. Actually, products such as cultured epidermis or cultured cartilage in which autologous cells are used have been commercially available.

A cell structure, which contains cells and macromolecular blocks having biocompatibility, and in which the plurality of the above-described macromolecular blocks are arranged in gaps between the plurality of the above-described cells, is disclosed in WO2011/108517A. In the cell structure disclosed in WO2011/108517A, it is possible to deliver nutrients to the inside of the cell structure from the outside. The cell structure has a sufficient thickness, and cells exist in the structure uniformly. In example of WO2011/108517A, high cell survival activity is verified using a macromolecular block formed of a recombinant gelatin material or a natural gelatin material. In addition, a cell structure for cell transplantation, which contains a macromolecular block having biocompatibility and at least one kind of cell, and in which the plurality of the above-described macromolecular blocks are arranged in the gaps between the plurality of the above-described cells, is disclosed in JP2014-12114A. Furthermore, a cell structure for cell transplantation which contains a biocompatible macromolecular block, containing no glutaraldehyde, and at least one kind of cell and in which a plurality of macromolecular blocks are arranged in gaps between a plurality of cells, and the tap density of the biocompatible macromolecular block is 10 mg/cm$^3$ to 500 mg/cm$^3$ or a value of the square root of the cross-sectional area circumference length in a two-dimensional cross-sectional image of the macromolecular block is 0.01 to 0.13 is disclosed in WO2014/133081A.

SUMMARY OF THE INVENTION

In producing cell structures disclosed in WO2011/108517A, JP2014-12114A and WO2014/133081A, there is a case where it is desired to further shorten the time for constructing a cell structure having a desired size depending on the type of cell to be used, or a case where it is desired to form a bigger three-dimensional cell structure. An object of the present invention is to provide a cell structure which can be produced within a short period of time and has a size larger than a predetermined size. Furthermore, another object of the present invention is to provide a method for producing the above-described cell structure.

The present inventors have conducted extensive studies in order to solve the above-described problems. As a result, they have succeeded in producing a cell structure having a size larger than or equal to a predetermined size within a short period of time using a combination of a first cell requiring a relatively long time to form a cell structure which contains a biocompatible macromolecular block and a cell and in which a plurality of biocompatible macromolecular blocks are arranged in gaps between a plurality of cells, and a second cell which has a strong adhesive force to a base material and easily forms a cell aggregation. The present invention has been completed based on these findings.

That is, according to the present invention, the following inventions are provided.

(1) A cell structure comprising: a biocompatible macromolecular block; and two or more kinds of cells, in which a plurality of the biocompatible macromolecular blocks are arranged in gaps between a plurality of the cells, and in which the two or more kinds of cells contain at least one kind of first cell selected from the group consisting of vascular endothelial cells, cardiac muscle cells, pancreatic islet cells, liver cells, epithelial cells, endothelial cells, nerve cells, embryonic stem cells, induced pluripotent stem cells, corneal epithelial cells, and retinal pigment epithelial cells, and at least one kind of second cell selected from the group consisting of mesenchymal cells, stromal cells, fibroblasts, smooth muscle cells, myoblasts, mesenchymal stem cells, adipose-derived stem cells, and umbilical cord-derived stem cells.

(2) The cell structure according to (1), in which a ratio of the number of cells of the first cell to the second cell is 9:1 to 1:99.

(3) The cell structure according to (1) or (2), in which a size of the biocompatible macromolecular block is 10 μm to 300 μm.

(4) The cell structure according to any one of (1) to (3), in which a thickness or a diameter of the cell structure is 400 μm to 3 cm.

(5) The cell structure according to any one of (1) to (4), in which a tap density of the biocompatible macromolecular block is 10 mg/cm$^3$ to 500 mg/cm$^3$.

(6) The cell structure according to any one of (1) to (5), in which a biocompatible macromolecule is cross-linked in the biocompatible macromolecular block.

(7) The cell structure according to (6), in which the cross-linking degree of the biocompatible macromolecular block is greater than or equal to 2, and the water absorption rate of the biocompatible macromolecular block is greater than or equal to 300%.

(8) The cell structure according to any one of (1) to (7), in which the biocompatible macromolecular block is obtained by pulverizing a solid matter containing a biocompatible macromolecule.

(9) The cell structure according to (8), in which the solid matter is obtained by freeze-drying an aqueous solution containing a biocompatible macromolecule.

(10) The cell structure according to any one of (1) to (9), in which 0.0000001 μg to 1 μg of the biocompatible macromolecular block is contained per cell.

(11) The cell structure according to any one of (1 to (10), in which the biocompatible macromolecule is recombinant gelatin.

(12) The cell structure according to (11), in which the recombinant gelatin is represented by the following formula

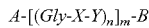

Formula:

(where A represents an arbitrary amino acid or an amino acid sequence, B represents an arbitrary amino acid or an amino acid sequence, n pieces of X each independently represent any amino acid, n pieces of Y each independently represent any amino acid, n represents an integer of 3 to 100, and m represents an integer of 2 to 10. n pieces of Gly-X-Y may be the same as or different from each other.)

(13) The cell structure according to (11) or (12), in which the recombinant gelatin is any of a peptide formed of an amino acid sequence described in SEQ ID No: 1; a peptide which is formed of an amino acid sequence in which one or several amino acids are deleted, substituted, or added in the amino acid sequence described in SEQ ID No: 1, and has biocompatibility; and a peptide which is formed of an amino acid sequence having 80% or more sequence identity to the amino acid sequence described in SEQ ID No: 1, and has biocompatibility.

(14) The cell structure according to any one of (1) to (13), in which the first cell is a vascular endothelial cell or a liver cell, and the second cell is a fibroblast, a smooth muscle cell, or a mesenchymal stem cell.

(15) A method for producing the cell structure according to any one of (1) to (14), comprising: incubating a mixture of a biocompatible macromolecular block and a culture solution containing two or more kinds of cells, in which the two or more kinds of cells contain at least one kind of first cell selected from the group consisting of vascular endothelial cells, cardiac muscle cells, pancreatic islet cells, liver cells, epithelial cells, endothelial cells, nerve cells, embryonic stem cells, induced pluripotent stem cells, corneal epithelial cells, and retinal pigment epithelial cells, and at least one kind of second cell selected from the group consisting of mesenchymal cells, stromal cells, fibroblasts, smooth muscle cells, myoblasts, mesenchymal stem cells, adipose-derived stem cells, and umbilical cord-derived stem cells.

(16) The method according to (15), in which the ratio of the number of cells of the first cell to the second cell in the culture solution containing two or more kinds of cells is 9:1 to 1:99.

The cell structure of the present invention can be produced within a short period of time and has a size larger than a predetermined size. In addition, according to the method for producing a cell structure, it is possible to produce the cell structure having a size larger than or equal to a predetermined size within a short period of time.

BRIEF DESCRIPTION OF THE DRAWINGS

FIG. 12 shows a formation of a mosaic cell aggregation of a HUVEC cell (human umbilical vein endothelial cell) and BdSMC (normal human bladder smooth muscle cell).

DESCRIPTION OF THE PREFERRED EMBODIMENTS

Figure 1:
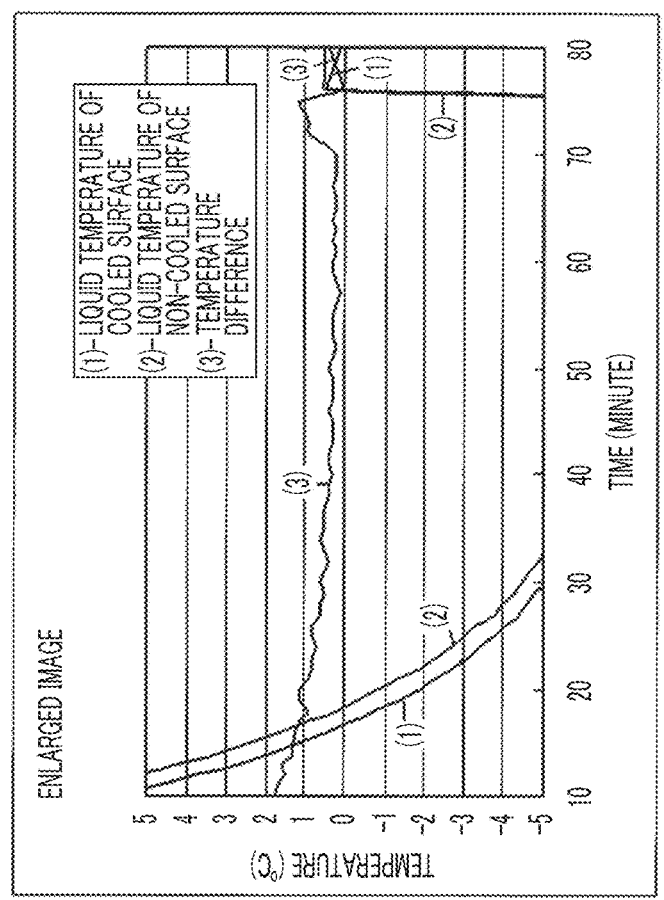
FIG. 1 shows a liquid temperature profile of a condition A of examples.
Figure 1:
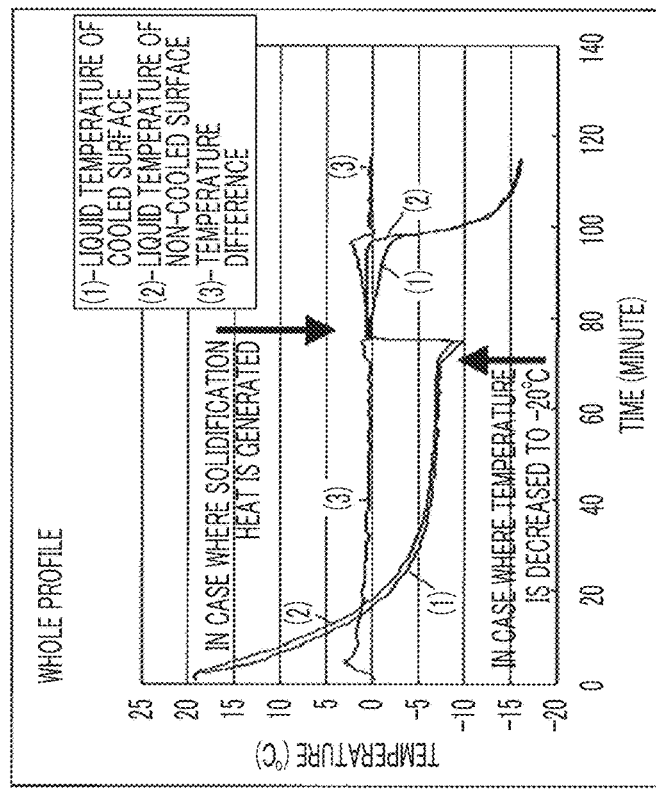

Hereinafter, an embodiment of the present invention will be described in detail.

The present invention relates to a cell structure including: a biocompatible macromolecular block; and two or more kinds of cells, in which a plurality of the biocompatible macromolecular blocks are arranged in gaps between a plurality of the cells, and in which the two or more kinds of cells contain at least one kind of first cell selected from the group consisting of vascular endothelial cells, cardiac muscle cells, pancreatic islet cells, liver cells, epithelial cells, endothelial cells, nerve cells, embryonic stem cells, induced pluripotent stem cells, corneal epithelial cells, and retinal pigment epithelial cells, and at least one kind of second cell selected from the group consisting of mesenchymal cells, stromal cells, fibroblasts, smooth muscle cells, myoblasts, mesenchymal stem cells, adipose-derived stem cells, and umbilical cord-derived stem cells. In some cases, the cell structure of the present invention is called a mosaic cell aggregation (a cell aggregation in a mosaic shape) in the present specification.

In the present invention, the first cell is a cell requiring a relatively long time to form a cell structure, and the second cell is a cell which has a strong adhesive force to a base material and easily forms a cell aggregation. In the present invention, it is possible to produce a cell structure having a size larger than or equal to a predetermined size within a short period of time using a combination of the first cell and the second cell, compared to a case where a cell structure is produced using only the first cell.

Being "capable of producing a cell structure having a size larger than or equal to a predetermined size within a short period of time" means that it is possible to produce a cell structure having a size larger than or equal to a predetermined size within a short period of time using a combination of the first cell and the second cell, compared to the case where a cell structure is produced using only the first cell, and the "size larger than or equal to a predetermined size" and the "short period of time" are not particularly limited. An example of being "capable of producing a cell structure having a size larger than or equal to a predetermined size within a short period of time" include a degree capable of forming a cell structure having a diameter within 1.5 mm in a case of being viewed from above within 1 day (24 hours) in a case of producing a spherical body having a diameter of about 1 mm within 1 well of a non-cell-adhesive U-shaped 96-well plate using $2 \times 10^4$ cells and 0.02 mg of biocompatible macromolecular blocks. However, the above-described experimental conditions are an example, and the scope of the present invention is not limited to the conditions.

Being capable of producing a cell structure having a size larger than or equal to a predetermined size within a short period of time using a combination of the first cell and the second cell, compared to the case where a cell structure is produced using only the first cell as described above is a finding first found by the present invention, and is completely unexpected from the related art.

It is considered from the results of the present invention that the first cell and the second cell can be classified by factors such as the strength of a cell-cell interaction and the strength of a cell-base material interaction, and depending on whether cells are easily laminated even in the cell-cell interaction. The cell group classified as the second cell may be excellent in all of the above-described three viewpoints, and therefore, it is considered that the cell group classified as the second cell plays a role as an adhesive between the first cells or between the first cell and the base material after the first cell forms a cell structure. That is, it is considered that since the second cell plays a role as a strong adhesive and strengthens an adhesive force necessary for forming the cell structure, the formation of the cell structure as an aggregate is successfully accelerated.

(1) Biocompatible Macromolecular Block (1-1) Biocompatible Macromolecules

Biocompatibility means a property which does not cause a significantly harmful reaction such as a long-term and chronic inflammatory reaction, during contact with a living body. Whether or not the biocompatible macromolecules used in the present invention are decomposed within a living body is not particularly limited as long as the biocompatible macromolecules have affinity to the living body. However, biodegradable macromolecules are preferable. Specific examples of non-biodegradable materials include polytetrafluoroethylene (PTFE), polyurethane, polypropylene, polyester, vinyl chloride, polycarbonate, acryl, stainless steel, titanium, silicone, and 2-methacryloyloxyethyl phosphorylcholine (MPC). Specific examples of the biodegradable materials include polypeptide (for example, gelatin or the like to be described below) such as recombinant peptide or chemically synthesized peptide, polylactic acid, polyglycolic acid, lactic acid-glycolic acid copolymers (PLGA), hyaluronic acid, glycosaminoglycan, proteoglycan, chondroitin, cellulose, agarose, carboxymethyl cellulose, chitin, and chitosan. Among these, recombinant peptide is particularly preferable. Devising of an improvement of cell adhesion properties in these biocompatible macromolecules may be performed. Specifically, methods such as 1. "coating of the surface of a base material with a cell adhesion substrate (fibronectin, vitronectin, or laminin) or peptides of a cell adhesion sequence (an RGD sequence, an LDV sequence, an REDV sequence (SEQ ID No: 2), a YIGSR sequence (SEQ ID No: 3), a PDSGR sequence (SEQ ID No: 4), an RYVVLPR sequence (SEQ ID No: 5), an LGTIPG sequence (SEQ ID No: 6), an RNIAEIIKDI sequence (SEQ ID No: 7), an IKVAV sequence (SEQ ID No: 8), an LRE sequence, a DGEA sequence (SEQ ID No: 9), and a HAV sequence, which are represented by one-letter notation of amino acids)", "aminization or cationization of the surface of a base material", or "plasma treatment performed on the surface of a base material or hydrophilic treatment due to corona discharge" can be used.

The kind of polypeptide containing a recombinant peptide or a chemically synthesized peptide is not particularly limited as long as a polypeptide has biocompatibility. For example, gelatin, collagen, elastin, fibronectin, ProNectin, laminin, tenascin, fibrin, fibroin, entactin, thrombospondin, and RetroNectin are preferable and gelatin, collagen, and atelocollagen are most preferable. As the gelatin to be used in the present invention, natural gelatin, recombinant gelatin, or chemically synthesized gelatin is preferable and recombinant gelatin is more preferable. The natural gelatin referred to herein means gelatin produced using naturally derived collagen.

The chemically synthesized peptide or the chemically synthesized gelatin means an artificially synthesized peptide or gelatin. The synthesis of a peptide such as gelatin may be solid phase synthesis or liquid phase synthesis, but is preferably solid phase synthesis. The solid phase synthesis of a peptide is well-known to those skilled in the art, and examples thereof include a fluorenyl-methoxy-carbonyl group (Fmoc group) synthesis method in which a Fmoc group is used for protection of an amino group, and a tert-butyl oxy carbonyl group (Boc group) synthesis method in which a Boc group is used for protection of an amino group. As a preferred embodiment of the chemically synthesized gelatin, it is possible to apply the contents in (1-3) Recombinant Gelatin to be described below in the present specification.

The recombinant gelatin will be described below in the present specification.

A "1/IOB" value which is a hydrophilic value of biocompatible macromolecules used in the present invention is preferably within a range of 0 to 1.0, more preferably within a range of 0 to 0.6, and still more preferably within a range of 0 to 0.4. IOB is an index of hydrophilic and hydrophobic properties based on an organic conceptual diagram representing polarity and non-polarity of an organic compound proposed by Atsushi HUJITA, and the details thereof are described in, for example, "Pharmaceutical Bulletin", vol. 2, 2, pp. 163-173 (1954), "Area of Chemistry" vol. 11, 10, pp. 719-725 (1957), and "Fragrance Journal", vol. 50, pp. 79-82 (1981). Briefly, the root of every organic compound is set to methane ($CH_4$), and all of other compounds are regarded as derivatives of methane. Certain numerical values for the number of carbons thereof, a substituent group, a transformation portion, a ring, and the like are set, and an organic value (OV) and an inorganic value (IV) are obtained by adding the score thereof. These values are plotted on a diagram in which the organic value is shown on the X-axis and the inorganic value is shown on the Y-axis. IOB in the organic conceptual diagram refers to a ratio of the inorganic value (IV) to the organic value (OV) in the organic conceptual diagram, that is, "inorganic value (IV)/organic value (OV)". The details of the organic conceptual diagram can be referred to "New Edition Organic Conceptual Diagram—Foundation and Application—" (written by Yoshio KOUDA, Sankyo Shuppan Co., Ltd., 2008). In the present specification, the hydrophilic and hydrophobic properties are represented by a "1/IOB" value which was obtained by taking a reciprocal number of JOB. This is a notation of representing more hydrophilic properties as the "1/IOB" value becomes small (close to 0).

The hydrophilic properties and water absorbency become high by making the "1/IOB" value of the macromolecules used in the present invention be within the above-described range, which effectively acts to hold nutrient components.

In a case where the biocompatible macromolecules used in the present invention are polypeptides, the hydrophilic and hydrophobic indexes represented by a grand average of hydropathicity (GRAVY) value is preferably −9.0 to 0.3, and more preferably −7.0 to 0.0. The grand average of hydropathicity (GRAVY) value can be obtained through "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi I., Appeal R. D., Bairoch A.; ExPASy: the proteomics server for in-depth protein knowledge and analysis.; Nucleic Acids Res. 31:3784-3788 (2003)".

The hydrophilic properties and water absorbency become high by making the GRAVY value of the macromolecules used in the present invention be within the above-described range, which effectively acts to hold nutrient components.

(1-2) Cross-Linking

The biocompatible macromolecules used in the present invention may be or may not be cross-linked, but are preferably cross-linked. By using the cross-linked biocompatible macromolecules, it is possible to obtain an effect of preventing instant decomposition during culturing in a medium and during transplantation into a living body. As general cross-linking methods, thermal cross-linking, cross-linking using aldehydes (for example, formaldehyde or glutaraldehyde), cross-linking using a condensation agent (carbodiimide, cyanamide, or the like), enzymatic cross-linking, photocrosslinking, ultraviolet cross-linking, a hydrophobic interaction, hydrogen bonding, an ionic interaction, and the like are known, it is also possible to use the above-described cross-linking methods in the present invention. As the cross-linking methods used in the present invention, thermal cross-linking, ultraviolet cross-linking, or enzymatic cross-linking is more preferable, and thermal cross-linking is particularly preferable.

In a case of performing cross-linking using an enzyme, there is no particular limitation as long as the enzyme has a cross-linking action between macromolecular materials. However, it is possible to perform cross-linking preferably using transglutaminase and laccase and most preferably using transglutaminase. Specific examples of protein to be subjected to enzymatic cross-linking using transglutaminase are not particularly limited as long as the protein has a lysine residue and a glutamine residue. Transglutaminase may be derived from a mammal or may be derived from a microorganism. Specific examples thereof include mammal-derived transglutaminase which has been sold as Activa series manufactured by Ajinomoto Co., Inc., and a reagent; guinea pig liver-derived transglutaminase manufactured by, for example, Oriental Yeast Co., Ltd., Upstate USA Inc., or Biodesign International, Inc.; goat-derived transglutaminase; rabbit-derived transglutaminase; and human-derived blood coagulation factors (Factor XIIIa: Haematologic Technologies, Inc).

The reaction temperature in a case of performing cross-linking (for example, thermal cross-linking) is not particularly limited as long as cross-linking can be performed, but is preferably −100° C. to 500° C., more preferably 0° C. to 300° C., still more preferably 50° C. to 300° C., still more preferably 100° C. to 250° C., and still more preferably 120° C. to 200° C.

(1-3) Recombinant Gelatin

The recombinant gelatin referred in the present invention means polypeptides or protein-like substances which have an amino acid sequence similar to that of gelatin produced through gene recombination technology. The recombinant gelatin which can be used in the present invention preferably has a repetition of a sequence (X and Y each independently show any amino acids) represented by Gly-X-Y which is characteristic to collagen. Here, a plurality of pieces of Gly-X-Y may be the same as or different from each other. Preferably, two or more sequences of cell adhesion signals are included in one molecule. As the recombinant gelatin used in the present invention, it is possible to use recombinant gelatin having an amino acid sequence derived from a partial amino acid sequence of collagen, and to use recombinant gelatin disclosed in, for example, EP1014176, U.S. Pat. No. 6,992,172B, WO2004/85473A, and WO2008/103041A. However, the recombinant gelatin is not limited thereto. Preferred recombinant gelatin used in the present invention is recombinant gelatin of the following aspect.

The recombinant gelatin is excellent in biocompatibility with original performance of natural gelatin, and is excellent in non-infection properties since there is no concern of bovine spongiform encephalopathy (BSE) and the recombinant gelatin with not being naturally derived. In addition, the recombinant gelatin is even compared to natural gelatin, and a sequence is determined. Therefore, it is possible to accurately design the strength and degradability so as to reduce deviation through cross-linking or the like.

The molecular weight of recombinant gelatin is not particularly limited, but is preferably 2,000 to 100,000 (2 kDa to 100 kDa), more preferably (2,500 to 95,000 (2.5 kDa to 95 kDa), still more preferably 5,000 to 90,000 (5 kDa to 90 kDa), and most preferably 10,000 to 90,000 (10 kDa to 90 kDa).

The recombinant gelatin preferably has a repetition of a sequence represented by Gly-X-Y which is characteristic to collagen. Here, a plurality of pieces of Gly-X-Y may be the same as or different from each other. In Gly-X-Y, Gly represents glycine and X and Y represent an arbitrary amino acid (preferably represents an arbitrary amino acid other than glycine). The sequence represented by Gly-X-Y characteristic to collagen is a partial structure which is extremely specific compared to other protein in a composition or a sequence of an amino acid of gelatin/collagen. In this section, glycine occupies about one third of the entirety of the amino acid sequence, one sequence is repeated every three sequences. Glycine is the simplest amino acid. Therefore, there is a little restraint in arrangement of molecular chains and glycine significantly contributes to regeneration of a helix structure during gelation. It is preferable that amino acids represented by X and Y contain many imino acids (proline and oxyproline) and occupy 10% to 45% of the entirety of the sequence. Preferably 80% or more of the sequence of the amino acids, more preferably 95% or more of the sequence of the amino acids, and most preferably 99% or more of the sequence of the amino acids in the recombinant gelatin has a repeating structure of Gly-X-Y.

In general gelatin, a polar amino acid with an electrical charge and a polar non-charged amino acid exist by 1:1 in polar amino acids. Here, the polar amino acid specifically indicates cysteine, aspartic acid, glutamic acid, histidine, lysine, asparagine, glutamine, serine, threonine, tyrosine, or arginine. Among these, the polar non-charged amino acid indicates cysteine, asparagine, glutamine, serine, threonine, or tyrosine. In recombinant gelatin used in the present invention, the proportion of the polar amino acid in the whole constituent amino acid is 10% to 40% and preferably 20% to 30%. It is preferable that the proportion of a non-charged amino acid in the polar amino acid is greater than or equal to 5% and less than 20% and preferably less than 10%. Furthermore, it is preferable that any one amino acid or preferably two or more amino acids among serine, threonine, asparagine, tyrosine, and cysteine are not contained on a sequence.

In general, in polypeptides, minimum amino acid sequences which work as cell adhesion signals are known (for example, Nagai Shoten Co., Ltd., "Pathophysiology", Vol. 9, No. 7 (1990) p. 527). The recombinant gelatin used in the present invention preferably has two or more these cell adhesion signals in one molecule. As the specific sequences, sequences such as an RGD sequence, an LDV sequence, an REDV sequence (SEQ ID No: 2), a YIGSR sequence (SEQ ID No: 3), a PDSGR sequence (SEQ ID No: 4), an RYVVLPR sequence (SEQ ID No: 5), an LGTIPG sequence (SEQ ID No: 6), an RNIAEIIKDI sequence (SEQ ID No: 7), an IKVAV sequence (SEQ ID No: 8), an LRE sequence, a DGEA sequence (SEQ ID No: 9), and a HAV sequence, which are represented by one-letter notation of amino acids are preferable in that there are many kinds of cells adhered. An RGD sequence, a YIGSR sequence (SEQ ID No: 3), a PDSGR sequence (SEQ ID No: 4), an LGTIPG sequence (SEQ ID No: 6), an IKVAV sequence (SEQ ID No: 8), and a HAV sequence are more preferable and an RGD sequence is particularly preferable. In the RGD sequence, an ERGD sequence (SEQ ID No: 10) is preferable. It is possible to improve the production amount of substrate of a cell using recombinant gelatin having cell adhesion signals. For example, it is possible to improve the production of glycosaminoglycan (GAG) in a case of cartilage differentiation using mesenchymal stem cells as cells.

As arrangement of RGD sequences in recombinant gelatin used in the present invention, it is preferable that the number of amino acids between RGDs is between 0 to 100 and preferably between 25 to 60 without being even.

The content of this minimum amino acid sequence is preferably 3 to 50, more preferably 4 to 30, and particularly preferably 5 to 20 in one molecule of protein in view of cell adhesion properties and proliferation properties. The most preferable content thereof is 12.

In recombinant gelatin used in the present invention, the proportion of RGD motifs with respect to the total number of amino acids is preferably at least 0.4%. In a case where recombinant gelatin contains 350 or more amino acids, each stretch of the 350 amino acids preferably contains at least one RGD motif. The proportion of RGD motifs with respect to the total number of amino acids is still more preferably at least 0.6%, still more preferably at least 0.8%, still more preferably at least 1.0%, still more preferably at least 1.2%, and most preferably at least 1.5%. The number of RGD motifs within a recombinant peptides is, per 250 amino acids, preferably at least 4, still more preferably 6, still more preferably 8, and still more preferably 12 to 16. The proportion of RGD motifs being 0.4% corresponds to at least one RGD sequence per 250 amino acids. The number of RGD motifs is an integer, and therefore, gelatin formed of 251 amino acids needs to contain at least two RGD sequences in order to satisfy the characteristics of 0.4%. It is preferable that the recombinant gelatin of the present invention contains at least two RGD sequences per 250 amino acids, more preferably contains at least three RGD sequences per 250 amino acids, and still more preferably contains at least four RGD sequences per 250 amino acids. As a further mode of the recombinant gelatin of the present invention, the recombinant gelatin contains at least four RGD motifs, preferably 6 RGD motifs, more preferably 8 RGD motifs, and still more preferably 12 to 16 RGD motifs.

In addition, the recombinant gelatin may be partially hydrolyzed.

The recombinant gelatin used in the present invention is preferably represented by Formula 1: A-[(Gly-X-Y)$_n$]$_m$-B. n pieces of X each independently represent any amino acid and n pieces of Y each independently represent any amino acid. m preferably represents an integer of 2 to 10 and more preferably represents an integer of 3 to 5. n is preferably an integer of 3 to 100, more preferably an integer of 15 to 70, and most preferably an integer of 50 to 65. A represents an arbitrary amino acid or an amino acid sequence, B represents an arbitrary amino acid or an amino acid sequence. n pieces of Gly-X-Y may be the same as or different from each other.

More preferably, the recombinant gelatin used in the present invention is represented by Formula: Gly-Ala-Pro-[(Gly-X-Y)$_{63}$]$_3$-Gly (where 63 pieces of X each independently represent any amino acid and 63 pieces of Y each independently represent any amino acid. 63 pieces of Gly-X-Y may be the same as or different from each other) and SEQ ID No: 11.

It is preferable that a plurality of sequence units of collagen which naturally exists are bonded to a repeating unit. Any naturally existing collagen referred to herein may be used as long as the collagen naturally exists, but is preferably I type collagen, II type collagen, III type collagen, IV type collagen, or V type collagen, and more preferably I type collagen, II type collagen, or III type collagen. According to another form, the above-described collagen is preferably derived from a human, cattle, a pig, a mouse, or a rat, and is more preferably derived from a human.

An isoelectric point of the recombinant gelatin used in the present invention is preferably 5 to 10, more preferably 6 to 10, and still more preferably 7 to 9.5. The measurement of the isoelectric point of the recombinant gelatin can be carried out by measuring the pH after passing a 1 mass % gelatin solution through a mixed crystal column of a cation-anion exchange resin above-described disclosed in isoelectric focusing method (refer to Maxey, C. R. (1976; Phitogr. Gelatin 2, Editor Cox, P. J. Academic, London, Engl.))

It is preferable that the recombinant gelatin is not deaminated.

It is preferable that the recombinant gelatin does not have a telopeptide.

It is preferable that the recombinant gelatin is a substantially pure polypeptide which is prepared using a nucleic acid encoding an amino acid sequence.

It is particularly preferable that the recombinant gelatin used in the present invention is any of
(1) a peptide formed of an amino acid sequence described in SEQ ID No: 1;

(2) a peptide which is formed of an amino acid sequence in which one or a plurality of amino acids are deleted, substituted, or added in the amino acid sequence described in SEQ ID No: 1, and has biocompatibility; or (3) a peptide which is formed of an amino acid sequence having 80% or more (more preferably 90% or more, particularly preferably 95% or more, and most preferably 98% or more) sequence identity to the amino acid sequence described in SEQ ID No: 1, and has biocompatibility.

"One or a plurality of" in the "amino acid sequence in which one or a plurality of amino acids are deleted, substituted, or added" preferably means 1 to 20 amino acids, more preferably means 1 to 10 amino acids, still more preferably means 1 to 5 amino acids, and particularly preferably means 1 to 3 amino acids.

The recombinant gelatin used in the present invention can be produced through gene recombination technology which is known to those skilled in the art, and can be produced in accordance with, for example, methods disclosed in EP1014176A2, U.S. Pat. No. 6,992,172B, WO2004/85473A, and WO2008/103041A. Specifically, a gene encoding an amino acid sequence of predetermined recombinant gelatin is acquired, the acquired gene is incorporated into an expression vector to produce a recombinant expression vector, and a transformant is produced by introducing the recombinant expression vector into an appropriate host. The recombinant gelatin is produced by culturing the obtained transformant in an appropriate medium. Therefore, it is possible to prepare the recombinant gelatin used in the present invention by collecting the recombinant gelatin produced from a culture product.

(1-4) Biocompatible Macromolecular Block

In the present invention, a block (aggregation) formed of the above-described biocompatible macromolecules is used.

The shape of the biocompatible macromolecular block in the present invention is not particularly limited. Examples thereof include an amorphous shape, a spherical shape, a particulate shape (granule), a powdery shape, a porous shape, a fibrous shape, a spindle shape, a flat shape, and a sheet shape. An amorphous shape, a spherical shape, a particulate shape (granule), a powdery shape, and a porous shape are preferable. The amorphous shape indicates that the shape of a surface is uneven, and indicates, for example, an object, such as rock, which has roughness. Examples of the above-described shapes are not distinct from each other. For example, in some cases, an example of a subordinate concept of the particulate shape (granule) is an amorphous shape.

The shape of the biocompatible macromolecular block in the present invention is not particularly limited as described above. However, the tap density is preferably 10 mg/cm$^3$ to 500 mg/cm$^3$, more preferably 20 mg/cm$^3$ to 400 mg/cm$^3$, still more preferably 40 mg/cm$^3$ to 220 mg/cm$^3$, and particularly preferably 50 mg/cm$^3$ to 150 mg/cm$^3$.

The tap density is a value indicating how much volume of block can be densely filled. It can be seen that, as the value becomes smaller, the block cannot be densely filled, that is, the structure of the block is complicated. It is considered that the tap density of the biocompatible macromolecular block indicates the complexity of a surface structure of the biocompatible macromolecular block and the amount of void formed in a case where biocompatible macromolecular blocks are collected as an aggregate. As the tap density becomes smaller, the void between macromolecular blocks becomes larger and a grafted region of a cell becomes larger. In addition, in a case where the tap density is not too small, the biocompatible macromolecular block can appropriately exist between cells and nutrients can be delivered into a cell structure in a case where the cell structure is produced, and therefore, it is considered that it is preferable that the tap density falls within the above-described range.

The tap density referred to in the present specification can be measured as follows. A container (with a cylindrical shape with a diameter of 6 mm and a length of 21.8 mm: a capacity of 0.616 cm$^3$) (hereinafter, described as a cap) is prepared for the measurement of the tap density. First, the mass of only a cap is measured. Thereafter, a funnel is attached to the cap, and blocks are poured from the funnel so as to be collected in the cap. After placing a sufficient amount of block, the cap portion is hit 200 times on a hard object such as a desk, the funnel is removed, and the blocks are leveled with a spatula. The mass is measured in a state where the cap is filled up with the blocks. The tap density can be obtained by calculating the mass of only the blocks from the difference between the mass of the cap filled up with the blocks and the mass of only the cap, and dividing the mass of only the blocks by the volume of the cap.

The cross-linking degree of the biocompatible macromolecular block in the present invention is not particularly limited, but is preferably greater than or equal to 2, more preferably 2 to 30, still more preferably 4 to 25, and particularly preferably 4 to 22.

The method for measuring the solid (the number of cross-linking times per molecule) of a macromolecular block is not particularly limited. However, the cross-linking degree can be measured, for example, through a TNBS (2,4,6-trinitrobenzene sulfonic acid) method in examples to be described below. Specifically, a sample obtained by mixing macromolecular blocks, a NaHCO$_3$ aqueous solution, and a TNBS aqueous solution, allowing the mixture to react for 3 hours at 37° C., and then, stopping the reaction, and a blank obtained by mixing macromolecular blocks, a NaHCO$_3$ aqueous solution, and a TNBS aqueous solution and stopping a reaction immediately after the mixing were prepared. The cross-linking degree (the number of cross-linking times per molecule) can be calculated from (Formula 2) and (Formula 3) by measuring each absorbance (345 nm) of the sample and the blank which have been diluted with pure water.

$$(As-Ab)/14{,}600 \times V/w \quad \text{(Formula 2)}$$

(Formula 2) represents the amount (molar equivalent) of lysine per 1 g of macromolecular blocks.

(where As represents the sample absorbance, Ab represents the blank absorbance, V represents the amount (g) reaction liquid, and w represents the mass (mg) of the macromolecular blocks.)

$$1-(\text{sample (Formula 2)/uncross-linked macromolecules (Formula 2)}) \times 34 \quad \text{(Formula 3)}$$

(Formula 3) represents the number of cross-linking times per molecule.

The water absorption rate of the biocompatible macromolecular block in the present invention is not particularly limited, but is preferably greater than or equal to 300%, more preferably greater than or equal to 400%, still more preferably greater than or equal to 500%, particularly preferably greater than or equal to 700%, and most preferably greater than or equal to 800%. The upper limit of the water absorption rate is not particularly limited, but is generally less than or equal to 4,000% or less than or equal to 2,000%.

The method for measuring the water absorption rate of the biocompatible macromolecular block is not particularly limited. However, the water absorption rate of the biocompatible macromolecular block can be measured, for example, through the method in examples to be described below. Specifically, a 3 cm×3 cm nylon mesh bag is filled with about 15 mg of biocompatible macromolecular blocks at 25° C. and is swollen in ion exchange water for 2 hours. Then, the biocompatible macromolecular blocks are dried with air for 10 minutes, and the mass is measured at each stage to obtain the water absorption rate according to (Formula 4).

Water absorption rate=$(w2-w1-w0)/w0$ (Formula 4)

(where w0 represents the mass of a material before water absorption, w1 represents the mass of an empty bag after water absorption, and w2 represents the mass of the entirety of the bag containing the material after water absorption.)

The size of one biocompatible macromolecular block in the present invention is not particularly limited, but is preferably 1 μm to 700 μm, more preferably 10 μm to 700 μm, still more preferably 10 μm to 300 μm, still more preferably 20 μm to 200 μm, still more preferably 20 μm to 150 μm, and particularly preferably 53 μm to 106 μm. It is possible to favorably deliver nutrients into a cell structure from the outside by setting the size of one biocompatible macromolecular block to be within the above-described range. The size of one biocompatible macromolecular block does not mean that an average value of the sizes of a plurality of biocompatible macromolecular blocks is within the above-described range, but means the size of each biocompatible macromolecular block which is obtained by sieving a plurality of biocompatible macromolecular blocks.

The size of one block can be defined by the size of a sieve used in a case of dividing the block. For example, blocks remaining on a sieve with 106 μm in a case where blocks which have been passed through a sieve with 180 μm for sifting are sifted using the sieve with 106 μm can be regarded as blocks having a size of 106 to 180 μm. Next, blocks remaining on a sieve with 53 μm in a case where blocks which have been passed through the sieve with 106 μm for sifting are sifted using the sieve with 53 μm can be regarded as blocks having a size of 53 to 106 μm. Next, blocks remaining on a sieve with 25 μm in a case where blocks which have been passed through the sieve with 53 μm for sifting are sifted using the sieve with 25 μm can be regarded as blocks having a size of 25 to 53 μm.

(1-5) Method for Producing Biocompatible Macromolecular Block

The method for producing a biocompatible macromolecular block is not particularly limited. For example, it is possible to obtain a biocompatible macromolecular block by pulverizing a solid matter (such as a porous body of a biocompatible macromolecule) containing a biocompatible macromolecule using a pulverizer (such as NEW POWER-MILL). The solid matter (such as a porous body of a biocompatible macromolecule) containing a biocompatible macromolecule can be obtained, for example, by freeze-drying an aqueous solution containing the biocompatible macromolecule.

It is possible to produce an amorphous biocompatible macromolecular block of which the shape of the surface is uneven, by pulverizing a solid matter containing a biocompatible macromolecule as described above.

An example of the method for producing a porous body of a biocompatible macromolecule include a method including (a) a step of cooling a solution of biocompatible macromolecules under the conditions where the difference between the temperature of a portion having the highest liquid temperature within the solution and the temperature of a portion having the lowest liquid temperature within the solution is lower than or equal to 2.5° C. and the temperature of a portion having the highest liquid temperature within the solution is lower than or equal to a melting point, to an unfrozen state, (b) a step of freezing the solution of the biocompatible macromolecules obtained in the step (a), and (c) a step of freeze-drying the frozen biocompatible macromolecules obtained in the step (b).

In a case where the solution of the biocompatible macromolecules is cooled to an unfrozen state, the variation in the size of obtained porous pores is reduced by making the difference between the temperature of a portion having the highest liquid temperature and the temperature of a portion having the lowest liquid temperature within the solution be lower than or equal to 2.5° C. (preferably lower than or equal to 2.3° C. and more preferably lower than or equal to 2.1° C.), that is, by reducing the difference in temperature. The lower limit of the difference between the temperature of a portion having the highest liquid temperature and the temperature of a portion having the lowest liquid temperature within the solution is not particularly limited, but may be higher than or equal to 0° C. For example, the lower limit thereof may be higher than or equal to 0.1° C., higher than or equal to 0.5° C., higher than or equal to 0.8° C., or higher than or equal to 0.9° C.

The cooling in the step (a) is preferably carried out, for example, using a material (preferably TEFLON (registered trademark)) having a lower thermal conductivity than water. The portion having the highest liquid temperature within the solution can be supposed as the farthest portion from a cooling side, and the portion having the lowest liquid temperature within the solution can be supposed as a liquid temperature of the cooling surface.

In the step (a), the difference between the temperature of a portion having the highest liquid temperature within the solution and the temperature of a portion having the lowest liquid temperature within the solution immediately before generation of solidification heat is preferably lower than or equal to 2.5° C., more preferably lower than or equal to 2.3° C., and still more preferably lower than or equal to 2.1° C. Here, the "difference in temperature immediately before the generation of solidification heat" means a difference in temperature in a case where the difference in temperature becomes largest between 1 second and 10 seconds before the generation of solidification heat.

In the step (a), the temperature of a portion having the lowest liquid temperature within the solution is preferably lower than or equal to a melting point of a solvent −5° C., more preferably lower than or equal to a melting point of a solvent −5° C. and higher than or equal to a melting point of a solvent −20° C., and still more preferably lower than or equal to a melting point of a solvent −6° C. and higher than or equal to a melting point of a solvent −16° C. The solvent of a melting point of a solvent is a solvent of a solution of biocompatible macromolecules.

In the step (b), the solution of the biocompatible macromolecules obtained in the step (a) is frozen. The cooling temperature for the freezing in the step (b) is not particularly limited. Depending on cooling equipments, the cooling temperature is preferably a temperature which is 3° C. to 30° C. lower than the temperature of a portion having the lowest liquid temperature within the solution, more preferably a temperature which is 5° C. to 25° C. lower than the temperature of a portion having the lowest liquid temperature within the solution, and still more preferably a temperature which is 10° C. to 20° C. lower than the temperature of a portion having the lowest liquid temperature within the solution.

In the step (c), the frozen biocompatible macromolecules obtained in the step (b) are freeze-dried. The freeze-drying can be performed through a usual method. For example, the freeze-drying can be performed by carrying out vacuum drying at a temperature lower than a melting point of a solvent and further carrying out vacuum drying at room temperature (20° C.).

In the present invention, a biocompatible macromolecular block can be preferably produced by pulverizing the porous body obtained in the above-described step (c).

(2) Cell

The cell structure of the present invention contains two or more kinds of cells. In the present invention, at least one kind of first cell selected from the group consisting of vascular endothelial cells, cardiac muscle cells, pancreatic islet cells, liver cells, epithelial cells, endothelial cells, nerve cells, embryonic stem (ES) cells, induced pluripotent stem (iPS) cells, corneal epithelial cells, and retinal pigment epithelial cells, and at least one kind of second cell selected from the group consisting of mesenchymal cells, stromal cells, fibroblasts, smooth muscle cells, myoblasts, mesenchymal stem (MSC) cells, adipose-derived stem cells, and umbilical cord-derived stem cells are used.

The cell to be used as the first cell may be one or more kinds, preferably one to three kinds, more preferably one or two kinds, and still more preferably one kind.

The cell to be used as the second cell may be one or more kinds, preferably one to three kinds, more preferably one or two kinds, and still more preferably one kind.

It is preferable that the first cell is a vascular endothelial cell or a liver cell and the second cell is a fibroblast, a smooth muscle cell, or a mesenchymal stem cell. In addition, still another example of the first cell include at least one kind of cell selected from the group consisting of muscle cells, pancreatic islet cells, liver cells, epithelial cells, endothelial cells, nerve cells, embryonic stem (ES) cells, induced pluripotent stem (iPS) cells, corneal epithelial cells, and retinal pigment epithelial cells.

A combination of the first cell which is a liver cell and the second cell which is a fibroblast or a mesenchymal stem cell is particularly preferable.

Each of the above-described cells means the broadest range of each term, and may be any of cells collected from a living body, cells obtained by subjecting the cells collected from a living body to an operation (such as a gene transfer operation), and cells (for example, cardiac muscle cells, nerve cells, and the like which have been differentiated and induced from iPS cells) obtained by transition from other cells.

Confirmation whether a cell (hereinafter, referred to as a target cell) is a predetermined cell described above can be performed by checking whether the target cell has a function of each cell. Alternately, the confirmation can also be performed by checking whether the target cell expresses a marker specific to each cell. However, the present invention is not limited thereto.

Cells to be used are preferably animal cells, more preferably vertebrate animal-derived cells, and particularly preferably human-derived cells. In addition, the cells may be derived from any one of autologous cells and heterologous cells.

For example, it is possible to suitably use cardiac muscle cells, smooth muscle cells, fibroblasts, and the like which are autologous and have been extracted from autologous cells and heterologous cells, in heart diseases such as severe heart failure and severe myocardial infarction. It is possible to transplant nerve cells into a cerebral ischemia or cerebral infarction site or to transplant vascular endothelial cells into a myocardial infarction site or a skeletal muscle ischemia site. Another example of the cells to be used includes cells to be used for cell transplantation for diabetic organ disorders. For example, there are cells for cell transplantation therapy in which diseases such as blood circulation disorders in the kidney, the pancreas, peripheral nerves, the eyes, and the limbs are intensively studied. Attempts have been made to transplant pancreatic islet cells into the pancreas with a decreased insulin secretion ability, and such cells can be used for the transplantation. Cells for transplantation can be appropriately selected as the first cell and the second cell described above also in other organs.

In the present invention, at least one kind of first cell selected from the group consisting of vascular endothelial cells, cardiac muscle cells, pancreatic islet cells, liver cells, epithelial cells, endothelial cells, nerve cells, embryonic stem (ES) cells, induced pluripotent stem (iPS) cells, corneal epithelial cells, and retinal pigment epithelial cells is a cell requiring a long time to form a cell structure. At least one kind of first cell selected from the group consisting of mesenchymal cells, stromal cells, fibroblasts, smooth muscle cells, myoblasts, mesenchymal stem (MSC) cells, adipose-derived stem cells, and umbilical cord-derived stem cells is a cell capable of forming a cell structure at a high speed. In the present invention, it is possible to produce a cell structure having a size larger than or equal to a predetermined size within a short period of time using a combination of the first cell and the second cell described above.

The ratio of the number of cells of the first cell to the second cell in the cell structure of the present invention is not particularly limited, but is preferably 9:1 to 1:99, more preferably 9:1 to 2:8, and still more preferably 8:2 to 2:8.

(3) Cell Structure

In the present invention, the cell structure can have a thickness suitable for cell transplantation by three-dimensionally arranging a plurality of biocompatible macromolecular blocks in gaps between a plurality of cells in a mosaic shape using the biocompatible macromolecular blocks and two or more kinds of cells. Furthermore, a cell structure in which cells evenly exist in the structure is formed by three-dimensionally arranging the biocompatible macromolecular blocks and the cells in a mosaic shape, and it is possible to deliver nutrients to the inside of the cell structure from the outside.

In the cell structure of the present invention, the plurality of biocompatible macromolecular blocks are arranged in gaps between the plurality of cells. Here, the "gaps between cells" is not necessarily a space closed by the constituent cells, and may be interposed by the cells. Gaps are not necessarily present between all of the cells, and there may be a place where cells are brought into contact with each other. The distance of gaps between cells through biocompatible macromolecular blocks, that is, the gap distance in a case of selecting a certain cell, and a cell existing in a shortest distance from the certain cell is not particularly limited. However, the distance is preferably the size of a biocompatible macromolecular block, and a favorable distance is also within the range of the favorable size of a biocompatible macromolecular block.

In addition, the biocompatible macromolecular blocks have a configuration of being interposed by the cells. However, there are not necessarily cells between all of the biocompatible macromolecular blocks, and there may be a place where biocompatible macromolecular blocks are brought into contact with each other. The distance between biocompatible macromolecular blocks through cells, that is, the distance in a case of selecting a biocompatible macromolecular block, and a biocompatible macromolecular block existing in a shortest distance from the biocompatible macromolecular block is not particularly limited. However, the distance is preferably the size of an aggregation of cells in a case where one or several cells to be used are gathered. For example, the size thereof is 10 µm to 1,000 µm, preferably 10 µm to 100 µm, and more preferably 10 µm to 50 µm.

The expressions such as "evenly exist", for example, the "cell structure in which cells evenly exist in the structure" is used in the present specification. However, the expression does not mean complete evenness, but means that it is possible to deliver nutrients to the inside of the cell structure from the outside.

The thickness or the diameter of the cell structure in the present invention can be set to a desired thickness. As the lower limit, being greater than or equal to 215 µm is preferable, being greater than or equal to 400 µm is more preferable, and being greater than or equal to 730 µm is most preferable. The upper limit of the thickness or the diameter is not particularly limited, but a general range in use is preferably less than or equal to 3 cm, more preferably less than or equal to 2 cm, and still more preferably less than or equal to 1 cm. In addition, the range of the thickness or the diameter of the cell structure is preferably 400 µm to 3 cm, more preferably 500 µm to 2 cm, and still more preferably 720 µm to 1 cm. By setting the thickness or the diameter of the cell structure to be within the above-described range, it is possible to favorably deliver nutrients into the cell structure from the outside.

In the cell structure of the present invention, a region formed of biocompatible macromolecular blocks and a region formed of cells are preferably arranged in a mosaic shape. The "thickness or the diameter of cell structure" in the present specification indicates the following. In a case of selecting a certain point A in the cell structure, the length of a line segment which divides the cell structure is set as a line segment A such that the distance from the external boundary of the cell structure becomes shortest within a straight line passing through the point A. A point A at which the line segment A thereof in the cell structure becomes longest is selected, and the length of the line segment A during the selection thereof is set as the "thickness or the diameter of the cell structure".

In the cell structure in the present invention, the ratio of a biocompatible macromolecular block to a cell is not particularly limited. However, it is preferable that the ratio of a biocompatible macromolecular block per cell is preferably 0.0000001 µg to 1 µg, more preferably 0.000001 µg to 0.1 µg, still more preferably 0.00001 µg to 0.01 µg, and most preferably 0.00002 µg to 0.006 µg. By setting the ratio of the biocompatible macromolecular blocks to the cells to be within the above-described range, it is possible to make the cells more evenly exist. By setting the lower limit to be within the above-described range, it is possible to exhibit an effect of the cells in a case of using the cells for a desired purpose. Moreover, by setting the upper limit to be within the above-described range, it is possible to supply components in arbitrarily existing biocompatible macromolecular blocks to cells. Here, the components in biocompatible macromolecular blocks are not particularly limited, but examples thereof include components contained in a medium to be described below.

(4) Method for Producing Cell Structure

The cell structure of the present invention can be produced by mixing a biocompatible macromolecular block with two or more kinds of cells. More specifically, the cell structure of the present invention can be produced by alternately arranging a biocompatible macromolecular block and the above-described cell. The production method is not particularly limited, but is preferably a method for forming a biocompatible macromolecular block, and then, mixing the biocompatible macromolecular block with the cells. Specifically, it is possible to produce the cell structure of the present invention by incubating a mixture of a biocompatible macromolecular block and a culture solution containing two or more kinds of cells. The cells described above in the present specification can be used as the two or more kinds of cells. In addition, the ratio of the number of cells of the first cell to the second cell in the above-described culture solution containing two or more kinds of cells is not particularly limited, but is preferably 9:1 to 1:99, more preferably 9:1 to 2:8, and still more preferably 8:2 to 2:8.

In the present invention, for example, in a liquid held by a container, a cell and a biocompatible macromolecular block which has been prepared in advance can be arranged in a mosaic shape in the container. It is preferable to promote or control the formation of a cell structure formed of a cell and a biocompatible macromolecular block through natural aggregation, natural fall, centrifugation, or agitation as means for the arrangement.

As the container to be used, a container formed of a low-adhesive cell material or a non-adhesive cell material is preferable and a container formed of polystyrene, polypropylene, polyethylene, glass, polycarbonate, or polyethylene terephthalate is more preferable. The shape of the bottom surface of a container is preferably a flat bottom shape, a U-shape, and a V-shape.

In the cell structure (mosaic cell aggregation) obtained through the above-described method, the cell structure having a desired size may be produced through a method, for example,
(a) merging cell structures (mosaic cell aggregations), which have been separately prepared, with each other, or
(b) increasing the volume of the structure under a differentiation medium or a proliferation medium.

The method for merging the cell structures with each other or the method for increasing the volume of the cell structure is not particularly limited.

For example, it is possible to increase the volume of the cell structure by exchanging a medium with a differentiation medium or a proliferation medium in a step of incubating a mixture of a biocompatible macromolecular block and a cell-containing culture solution. Preferably, it is possible to produce a cell structure in which cells evenly exist in the cell structure and which has a desired size, by further adding a biocompatible macromolecular block, in the step of incubating a mixture of a biocompatible macromolecular block and a cell-containing culture solution.

In a case where cell structures which have been separately prepared are merged with each other, it is possible to, for example, merge a plurality of cell structures which contains a plurality of biocompatible macromolecular blocks and a plurality of cells and in which one or a plurality of the above-described biocompatible macromolecular blocks are arranged in some or all of a plurality of gaps formed by the plurality of the above-described cells. A cell structure obtained by merging a plurality of cell structures of the present invention with each other as described in the above-described (a) is also within the scope of the present invention.

Preferred ranges of "(the kind, the size, or the like of) biocompatible macromolecular block", the "cell", the "gap between cells", "(the size or the like) of an obtained cell structure", the "ratio of a cell to a biocompatible macromolecular block", and the like according to the method for producing a cell structure of the present invention are the same as those described above in the present specification.

The thickness or the diameter of each cell structure before the above-described merging is preferably 10 µm to 1 cm, more preferably 10 µm to 2000 µm, still more preferably 15 µm to 1500 µm, and most preferably 20 µm to 1300 µm. The thickness or the diameter thereof after the merging is preferably 400 µm to 3 cm, more preferably 500 µm to 2 cm, and still more preferably 720 µm to 1 cm.

A specific example of the above-described method for producing a cell structure with a desired size by further adding a biocompatible macromolecular block includes a method for performing incubation by further adding a second biocompatible macromolecular block to a cell structure which contains a plurality of first biocompatible macromolecular blocks and a plurality of cells and in which one or a plurality of the above-described biocompatible macromolecular blocks are arranged in some or all of a plurality of gaps formed by the plurality of the above-described cells. Here, preferred ranges of "(the kind, the size, or the like of) biocompatible macromolecular block", the "cell", the "gap between cells", "(the size or the like) of an obtained cell structure", the "ratio of a cell to a biocompatible macromolecular block", and the like according to the method for producing a cell structure of the present invention are the same as those described above in the present specification.

Cell structures to be merged are preferably arranged at a distance of 0 to 50 µm, more preferably arranged at a distance of 0 to 20 µm, and still more preferably at a distance of 0 to 5 µm. In a case of merging the cell structures, it is considered that cells or substrates produced by the cells play a role as an adhesive through proliferation and extension of cells, thereby bonding the cell structures to each other. By setting the distance between the cell structures to be within the above-described range, the adhesion between the cell structures becomes easy.

The range of the thickness or the diameter of the cell structure obtained through the method for producing a cell structure of the present invention is preferably 400 µm to 3 cm, more preferably 500 µm to 2 cm, and still more preferably 720 µm to 1 cm.

The pace at which the second biocompatible macromolecular block is added to a cell structure in the case of performing incubation by further adding the second biocompatible macromolecular block to the cell structure is appropriately selected in accordance with the proliferation rate of cells to be used. Specifically, in a case where the pace at which the second biocompatible macromolecular block is added is fast, the cells move outside the cell structure, and therefore, the uniformity of the cells is deteriorated. In a case where the pace of the addition is slow, a place where the proportion of the cells increases is generated, and therefore, the uniformity of the cells is deteriorated. Thus, the pace of the addition is selected in consideration of the proliferation rate of cells to be used.

(5) Use of Cell Structure

The cell structure of the present invention can be used for cell transplantation. Specifically, the cell structure of the present invention can be used for the purpose of transplanting cells into sites with heart diseases such as severe heart failure and severe myocardial infarction and diseases such as cerebral ischemia and cerebral infarction. In addition, the cell structure of the present invention can also be used for diabetic diseases such as blood circulation disorders in the kidney, the pancreas, the liver, peripheral nerves, the eyes, and the limbs As the transplantation method, it is possible to use incision and injection, and a method using an endoscope. In the cell structure of the present invention, it is possible to reduce the size of the structure unlike a cell-transplanted substance such as a cell sheet, and therefore, it is possible to perform less invasive transplantation method such as transplantation performed through injection.

In addition, according to the present invention, there is provided a cell transplantation method including a step of transplanting the cell structure of the present invention into a patient who requires cell transplantation. In the cell transplantation method, the cell structure of the present invention described above is used. The suitable range of the cell structure is the same as described above.

According to the present invention, use of the cell structure of the present invention for producing a cell transplantation treatment agent is further provided. According to the present invention, the suitable range of the cell structure is the same as described above.

According to the present invention, a cell transplantation treatment agent containing the cell structure of the present invention is further provided. According to the present invention, the suitable range of the cell structure is the same as described above.

The present invention will be more specifically described using the following examples, but is not limited by the examples.

EXAMPLES

[Example 1] Recombinant Peptide (Recombinant Gelatin)

The following CBE3 (which is disclosed in WO2008/103041A) was prepared as recombinant peptides (recombinant gelatin).
CBE3:
Molecular weight: 51.6 kD
Structure: GAP[(GXY)$_{63}$]$_3$G
Number of amino acids: 571
RGD sequence: 12
Imino acid content: 33%

Almost 100% of amino acids have a repeating structure of GXY. In the amino acid sequence of CBE3, serine, threonine, asparagine, tyrosine, and cysteine are not included. CBE3 has an ERGD sequence (SEQ ID No: 10).
Isoelectric point: 9.34
GRAVY value: −0.682
1/IOB value: 0.323

Amino acid sequence (SEQ ID No: 1 in a sequence table) (which is the same as that of SEQ ID No: 3 in WO2008/103041A. However, X in the end is corrected to "P").

GAP (GAPGLQGAPGLQGMPGERGAAGLPGPKGERGDAGPKGADGA

PGAPGLQGMPGERGAAGLPGPKGERGDAGPKGADGAPGKDGVRGLAGPIG

PPGERGAAGLPGPKGERGDAGPKGADGAPGKDGVRGLAGPIGPPGPAGAP

GAPGLQGMPGERGAAGLPGPKGERGDAGPKGADGAPGKDGVRGLAGPP)$_3$

G

[Example 2] Production of Porous Body of Recombinant Peptide

[PTFE Thickness•Cylindrical Container]

A cylindrical cup-shaped polytetrafluoroethylene (PTFE) container with a bottom surface thickness of 3 mm, a diameter of 51 mm, a side surface thickness of 8 mm, and a height of 25 mm was prepared. In a case where the curved surface of the cylindrical cup is set as a side surface, the side surface is closed by PTFE with 8 mm and the bottom surface (circular shape of a flat plate) is also closed by PTFE with 3 mm. In contrast, the upper surface is in an open shape. Accordingly, the inner diameter of the cylindrical cup is set to 43 mm. Hereinafter, this container is referred to as a PTFE thickness•cylindrical container.

[Aluminum Glass Plate•Cylindrical Container]

A cylindrical cup-shaped aluminum container with a thickness of 1 mm and a diameter of 47 mm was prepared. In a case where the curved surface of the cylindrical cup is set as a side surface, the side surface is closed by aluminum with 1 mm and the bottom surface (circular shape of a flat plate) is also closed by aluminum with 1 mm. In contrast, the upper surface is in an open shape. In addition, TEFLON (registered trademark) with a thickness of 1 mm is evenly spread only in the inside of the side surface, and as a result, the inner diameter of the cylindrical cup becomes 45 mm. In addition, the bottom surface of this container enters a state where a 2.2 mm glass plate is joined to the bottom surface thereof on the outside of aluminum. Hereinafter, this container is referred to as an aluminum glass•cylindrical container.

[Freezing Step in which Difference in Temperature is Small, and Drying Step]

An aqueous CBE3 solution was made to flow into the PTFE thickness•cylindrical container and the aluminum glass plate•cylindrical container, and was cooled down from the bottom surface within a vacuum freeze dryer (TF5-85ATNNN: Takara Co., Ltd.) using a cooling shelf. A combination of the setting of the final concentration of the aqueous CBE3 solutions in the containers at this time, the amount of solution, and the temperature of the shelf was prepared as described below.

Condition A:

PTFE thickness•cylindrical container, final concentration of aqueous CBE3 solution of 4 mass %, amount of aqueous solution of 4 mL. As the setting for the temperature of the shelf, the temperature was cooled down until the temperature reaches −10° C., and then, freezing was performed for 1 hour at −10° C., for 2 hours at −20° C., for 3 hours at −40° C., and finally for 1 hour at −50° C. Thereafter, the frozen product was subjected to vacuum drying for 24 hours at −20° C. after the setting of the temperature of the shelf was returned to −20° C. After 24 hours, the temperature of the shelf was increased to 20° C. in a state in which the vacuum drying was continued as it was, and the vacuum drying was further performed for 48 hours at 20° C. until the vacuum degree was sufficiently decreased ($1.9 \times 10^5$ Pa). Then, the product was taken out of the vacuum freeze dryer. Accordingly, a porous body was obtained.

Condition B:

Aluminum•glass plate•cylindrical container, final concentration of aqueous CBE3 solution of 4 mass %, amount of aqueous solution of 4 mL. As the setting for the temperature of the shelf, the temperature was cooled down until the temperature reaches −10° C., and then, freezing was performed for 1 hour at −10° C., for 2 hours at −20° C., for 3 hours at −40° C., and finally for 1 hour at −50° C. Thereafter, the frozen product was subjected to vacuum drying for 24 hours at −20° C. after the setting of the temperature of the shelf was returned to −20° C. After 24 hours, the temperature of the shelf was increased to 20° C. in a state in which the vacuum drying was continued as it was, and the vacuum drying was further performed for 48 hours at 20° C. until the vacuum degree was sufficiently decreased ($1.9 \times 10^5$ Pa). Then, the product was taken out of the vacuum freeze dryer. Accordingly, a porous body was obtained.

Condition C:

PTFE thickness•cylindrical container, final concentration of aqueous CBE3 solution of 4 mass %, amount of aqueous solution of 10 mL. As the setting for the temperature of the shelf, the temperature was cooled down until the temperature reaches −10° C., and then, freezing was performed for 1 hour at −10° C., for 2 hours at −20° C., for 3 hours at −40° C., and finally for 1 hour at −50° C. Thereafter, the frozen product was subjected to vacuum drying for 24 hours at −20° C. after the setting of the temperature of the shelf was returned to −20° C. After 24 hours, the temperature of the shelf was increased to 20° C. in a state in which the vacuum drying was continued as it was, and the vacuum drying was further performed for 48 hours at 20° C. until the vacuum degree was sufficiently decreased ($1.9 \times 10^5$ Pa). Then, the product was taken out of the vacuum freeze dryer. Accordingly, a porous body was obtained.

[Measurement of Temperature in Each Freezing Step]

Regarding the conditions A to C, the liquid temperature of the surface of water in a center portion of a circle within a container was measured as the liquid temperature (non-cooled surface liquid temperature) of the farthest portion from a cooling side in a solution, and the liquid temperature of a bottom portion within the container was measured as the liquid temperature (cooled surface liquid temperature) of the closest portion to the cooling side in the solution.

Figure 2:
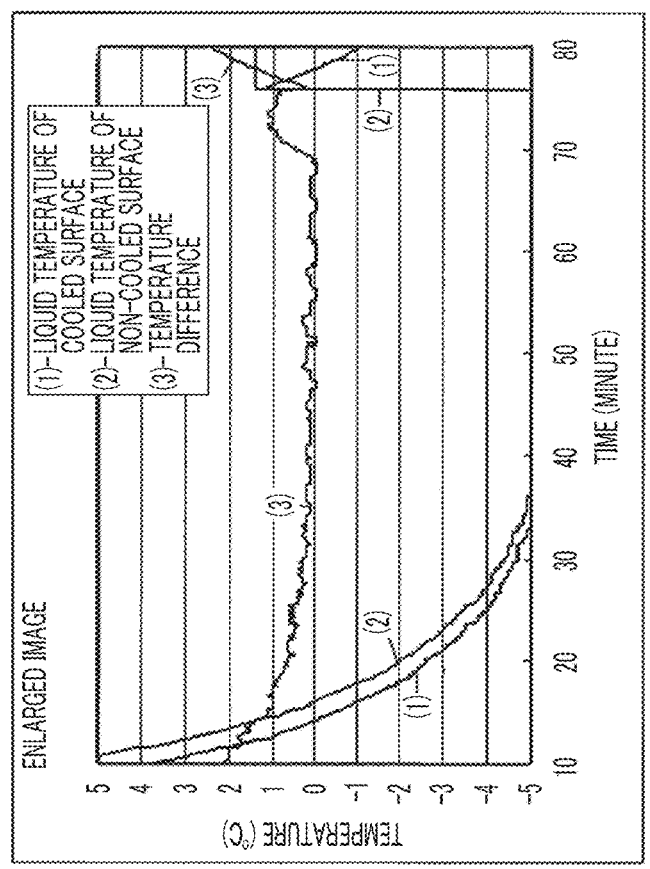
FIG. 2 shows a liquid temperature profile of a condition B of examples.
Figure 2:
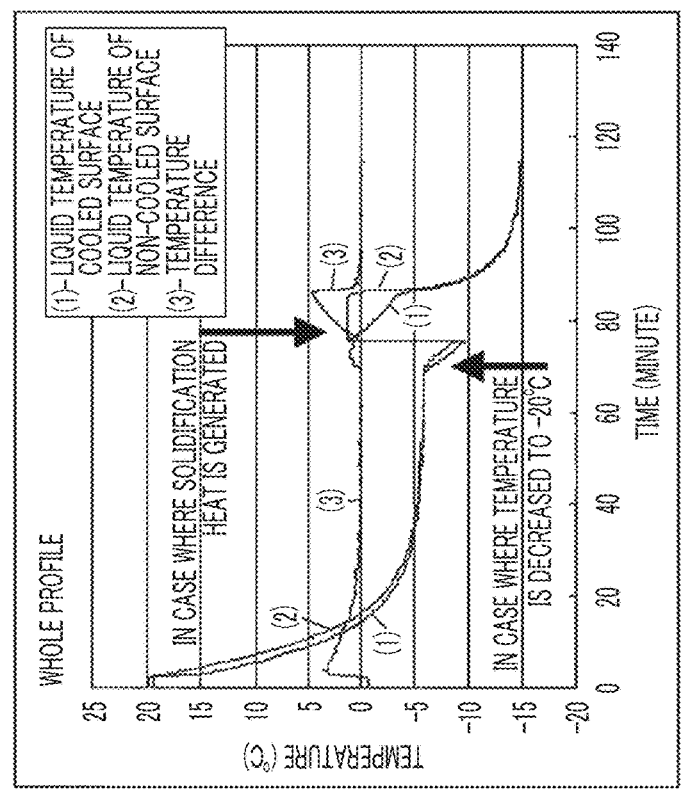
Figure 3:
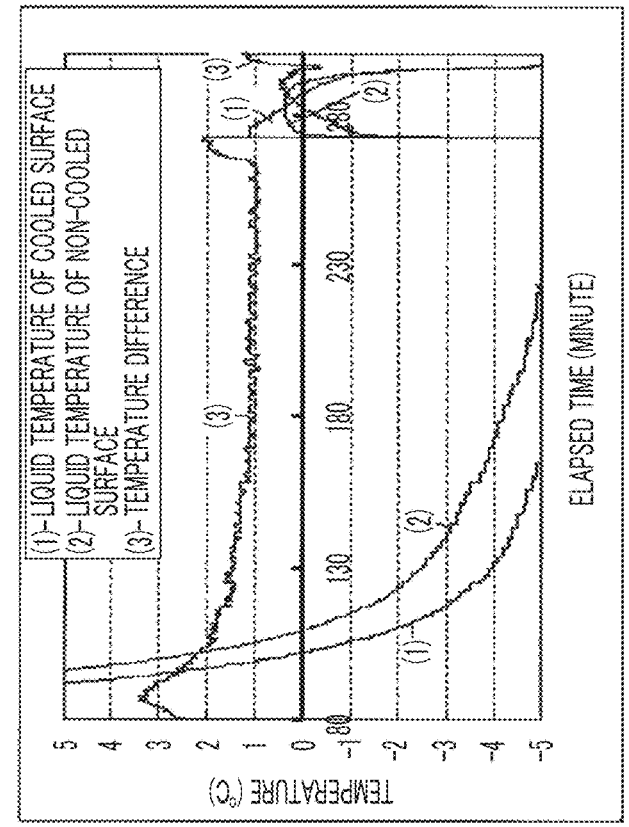
FIG. 3 shows a liquid temperature profile of a condition C of examples.
Figure 3:
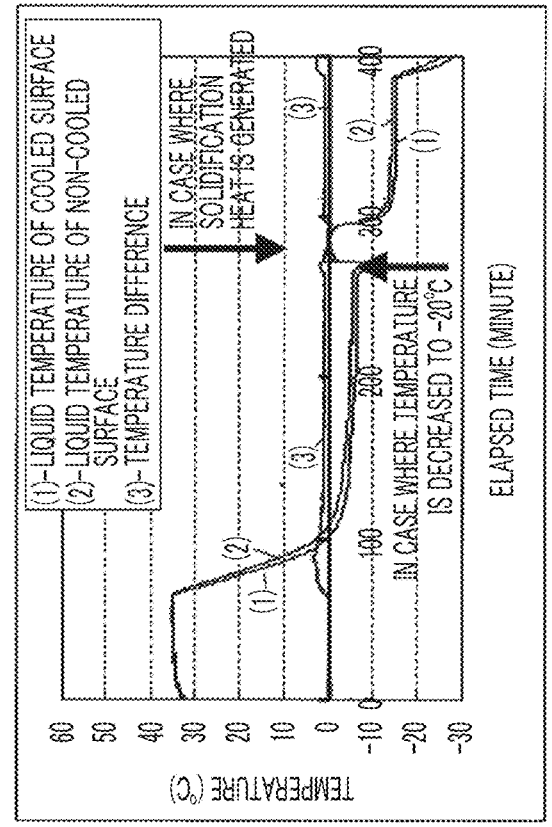

As a result, each temperature and a profile of the difference in temperature are as shown in FIGS. 1 to 3.

It can be seen from FIGS. 1 to 3 that the liquid temperature falls below 0° C., which is a melting point, in a setting section of the temperature of a shelf of −10° C. (before the temperature decreases to −20° C.) in the conditions A to C, and the solution enters a (unfrozen and overcooled) state where freezing does not occur in that state. In addition, in this state, the difference in temperature between the cooled surface liquid temperature and the non-cooled surface liquid temperature is less than or equal to 2.5° C. In the present specification, the "difference in temperature" means "non-cooled surface liquid temperature"—"cooled surface liquid temperature". Thereafter, the timing at which the liquid temperature rapidly rises to around 0° C. by further lowering the temperature of the shelf to −20° C. is confirmed. Here, it can be seen that freezing starts due to generation of solidification heat. In addition, it was also possible to confirm that ice formation actually started at the timing. Thereafter, the temperature was around 0° C. while the certain time passes. Here, the product entered a state where there was a mixture of water and ice. The temperature finally started to decrease again from 0° C. At this time, the liquid portion disappeared and became ice. Accordingly, the temperature being measured became a solid temperature within the ice, that is, was not the liquid temperature.

Hereinafter, regarding the conditions A to C, the difference in temperature at this time when the non-cooled surface liquid temperature became a melting point (0° C.), the difference in temperature immediately before the temperature of the shelf is decreased from −10° C. to −20° C., and the difference in temperature immediately before the generation of solidification heat will be described. The "difference in temperature immediately before" referred in the present invention indicates the highest temperature in the difference in temperature which can be detected between 1 second to 20 seconds before an event (such as the generation of solidification heat).

Condition A

Difference in temperature at this time when non-cooled surface liquid temperature became melting point (0° C.): 1.1° C.

Difference in temperature immediately before temperature is decreased from −10° C. to −20° C.: 0.2° C.

Difference in temperature immediately before generation of solidification heat: 1.1° C.

Condition B

Difference in temperature at this time when non-cooled surface liquid temperature became melting point (0° C.): 1.0° C.

Difference in temperature immediately before temperature is decreased from −10° C. to −20° C.: 0.1° C.

Difference in temperature immediately before generation of solidification heat: 0.9° C.

Condition C

Difference in temperature at this time when non-cooled surface liquid temperature became melting point (0° C.): 1.8° C.

Difference in temperature immediately before temperature is decreased from −10° C. to −20° C.: 1.1° C.

Difference in temperature immediately before generation of solidification heat: 2.1° C.

[Example 3] Production of Biocompatible Macromolecular Block (Pulverizing and Cross-Linking of Porous Body)

The CBE3 porous bodies which had been obtained in Example 2 were pulverized using NEW POWERMILL (Osaka Chemical Co., Ltd., NEW POWERMILL PM-2005). The pulverizing was performed for one minute×5 times, that is, for 5 minutes in total at the maximum rotation speed. The sizes of the obtained pulverized substances were divided using a stainless steel sieve to obtain uncross-linked blocks with 25 to 53 μm, 53 to 106 μm, and 106 to 180 μm. Thereafter, biocompatible macromolecular blocks (CBE3 blocks) were obtained by performing thermal cross-linking (six kinds of cross-linking times of 8 hours, 16 hours, 24 hours, 48 hours, 72 hours, and 96 hours) at 160° C. under reduced pressure.

Hereinafter, a porous body-derived block under the condition A which has been cross-linked for 48 hours is called E, and a porous body-derived block under the condition B which has been cross-linked for 48 hours is called F, E and F are blocks with a small difference in temperature which have been produced from porous bodies produced through a freezing step in which the difference in temperature is small. There was no influence of the difference in cross-linking time on the performance in the evaluation of the present specification. Therefore, the blocks cross-linked for 48 hours were representatively used. In addition, there was no difference in performance between E and F. Hereinafter, the biocompatible macromolecular blocks obtained in Example 3 are also referred to as "petal blocks". In Examples 4 to 7, biocompatible macromolecular blocks which have sizes of 53 to 106 μm, are produced under the condition A, and of which the cross-linking time is 48 hours were used.

[Example 4] Measurement of Tap Density of Biocompatible Macromolecular Block

The tap density is a value indicating how much volume of block can be densely filled. It can be said that, as the value becomes smaller, the block cannot be densely filled, that is, the structure of the block is complicated. The tap density was measured as follows. First, a funnel with an attached cap (having a cylindrical shape with a diameter of 6 mm and a length of 21.8 mm: capacity of 0.616 $cm^3$) at the tip thereof was prepared, and the mass of only the cap was measured. Thereafter, the cap was attached to the funnel, and blocks were poured from the funnel so as to be collected in the cap. After placing a sufficient amount of block, the cap portion was hit 200 times on a hard object such as a desk, the funnel was removed, and the blocks were leveled with a spatula. The mass was measured in a state where the cap was filled up with the blocks. The tap density was obtained by calculating the mass of only the blocks from the difference between the mass of the cap filled up with the blocks and the mass of only the cap, and dividing the mass of only the blocks by the volume of the cap.

As a result, the tap density of the biocompatible macromolecular blocks of Example 3 is 98 $mg/cm^3$.

[Example 5] Measurement of Cross-Linking Degree of Biocompatible Macromolecular Block The cross-linking degree (the number of cross-linking times per molecule) of the blocks cross-linked in Example 3 was calculated. The measurement was performed through a TNBS (2,4,6-trinitrobenzene sulfonic acid) method.

<Preparation of Sample>

A sample (about 10 mg), 4% $NaHCO_3$ aqueous solution (1 mL), and 1 mass % TNBS aqueous solution (2 mL) were added to a glass vial, and the mixture was shaken for 3 hours at 37° C. Thereafter, 37 mass % hydrochloric acid (10 mL) and pure water (5 mL) were added thereto, and then, the mixture was allowed to stand for 16 hours or longer at 37° C. to prepare a sample.

<Adjustment of Blank>

A blank (about 10 mg), 4 mass % $NaHCO_3$ aqueous solution (1 mL), and 1 mass % TNBS aqueous solution (2 mL) were added to a glass vial, 37 mass % hydrochloric acid (3 mL) was immediately added thereto, and the mixture was shaken for 3 hours at 37° C. Thereafter, 37 mass % hydrochloric acid (7 mL) and pure water (5 mL) were added thereto, and then, the mixture was allowed to stand for 16 hours or longer at 37° C. to prepare a blank.

The absorbance (345 nm) of the sample and the blank which had been diluted 10 times with pure water was measured, and the cross-linking degree (the number of cross-linking times per molecule) was calculated from (Formula 2) and (Formula 3).

$$(As-Ab)/14{,}600 \times V/w \qquad \text{(Formula 2)}$$

(Formula 2) represents the amount (molar equivalent) of lysine per 1 g of recombinant peptide.

(where As represents the sample absorbance, Ab represents the blank absorbance, V represents the amount (g) reaction liquid, and w represents the mass (mg) of recombinant peptide.)

$$1-(\text{sample (Formula 2)/uncross-linked recombinant peptide (Formula 2)}) \times 34 \qquad \text{(Formula 3)}$$

(Formula 3) represents the number of cross-linking times per molecule.

As a result, the cross-linking degree of the biocompatible macromolecular blocks of Example 3 is 4.2.

[Example 6] Measurement of Water Absorption Rate of Biocompatible Macromolecular Block The water absorption rate of biocompatible macromolecular blocks prepared in Example 3 was calculated.

A 3 cm×3 cm nylon mesh bag was filled with about 15 mg of the biocompatible macromolecular blocks at 25° C. and was swollen in ion exchange water for 2 hours. Then, the biocompatible macromolecular blocks were dried with air for 10 minutes, and the mass was measured at each stage to obtain the water absorption rate according to (Formula 4).

Water absorption rate=$(w2-w1-w0)/w0$    (Formula 4)

(where w0 represents the mass of a material before water absorption, w1 represents the mass of an empty bag after water absorption, and w2 represents the mass of the entirety of the bag containing the material after water absorption.)

As a result, the water absorption rate of the blocks of Example 3 is 786%.

[Example 7] Preparation of Cell Structure (Mosaic Cell Aggregation) Formed of Plurality of Kinds of Cells The total cell concentration of a cell suspension obtained by mixing a first cell and a second cell in a medium so as to obtain the ratio described in Table 1 below was adjusted so as to be $1 \times 10^5$ cells/mL using the medium. A medium for second cell culture was used as the medium. However, there was no change in the conclusion obtained even in a case of where a medium for first cell culture was used. MSCGM BulletKit™ of Lonza was used as a medium for MSC. FGM™-2 BulletKit™ of Lonza was used as a medium for NHDF. SmGM™-2 BulletKit™ of Lonza was used as a medium for BdSMC. EGM™-2 or EGM™ BulletKit™ of Lonza was used as a medium for HUVEC.

The biocompatible macromolecular blocks (53 to 106 μm) prepared in Example 3 was added to the above-described cell suspension so as to make a concentration of 0.1 mg/mL. 200 μL of the mixture obtained above was shown in a Sumilon Celltight X96U plate (of which the bottom was in a U-shape and was manufactured by Sumitomo Bakelite Co., Ltd.), and the plate was centrifuged in Mini Plate Centrifuge (600 g, 5 minutes) and was allowed to stand for 29 hours to prepare a mosaic cell aggregation (0.001 μg of biocompatible macromolecular blocks per cell) formed of fetal blocks and two kinds of cells. Changes over time for 29 hours were observed from the top of a U-shaped bottom well. Since the observation was performed from the top, the area of the cell aggregation viewed from the top gradually decreased (becoming more three-dimensional) in the process of forming the spherical mosaic cell aggregation. Photographs imaged while observing the change over time from the top are shown in FIGS. 4, 6, 8, 10, and 12. Graphs in which the diameter of the cell aggregation obtained by measuring the area of the cell aggregation and converting the area into a circle is plotted on a vertical axis and the elapsed time is plotted on a horizontal axis are shown in FIGS. 5, 7, 9, 11, and 12.

As the circular shape of the photographs becomes smaller, the mosaic cell aggregation is more rapidly formed. As the diameter of the vertical axis in the graphs more rapidly decreases, the mosaic cell aggregation is more rapidly formed.

Whether the diameter of the mosaic cell aggregation is within 1.5 mm when viewed from the top portion within 29 hours (hr) or whether the mosaic cell aggregation can be formed to have a small size larger than or equal to 0.5 mm from the size made of only a first cell can be considered as an indicator of the more rapid formation of the mosaic cell aggregation.

All of the diameters of the mosaic cell aggregations prepared in the present example are 1.0 mm to 3.0 mm.

In consideration of the proliferation rate of the cells used in the present example, each ratio of the number of cells of a first cell to a second cell in the mosaic cell aggregations after culture from 1 hour to 29 hours is substantially equivalent to the ratio (ratio described in Table 1) of the number of cells of a first cell to a second cell in the cell suspension.

Figure 4:
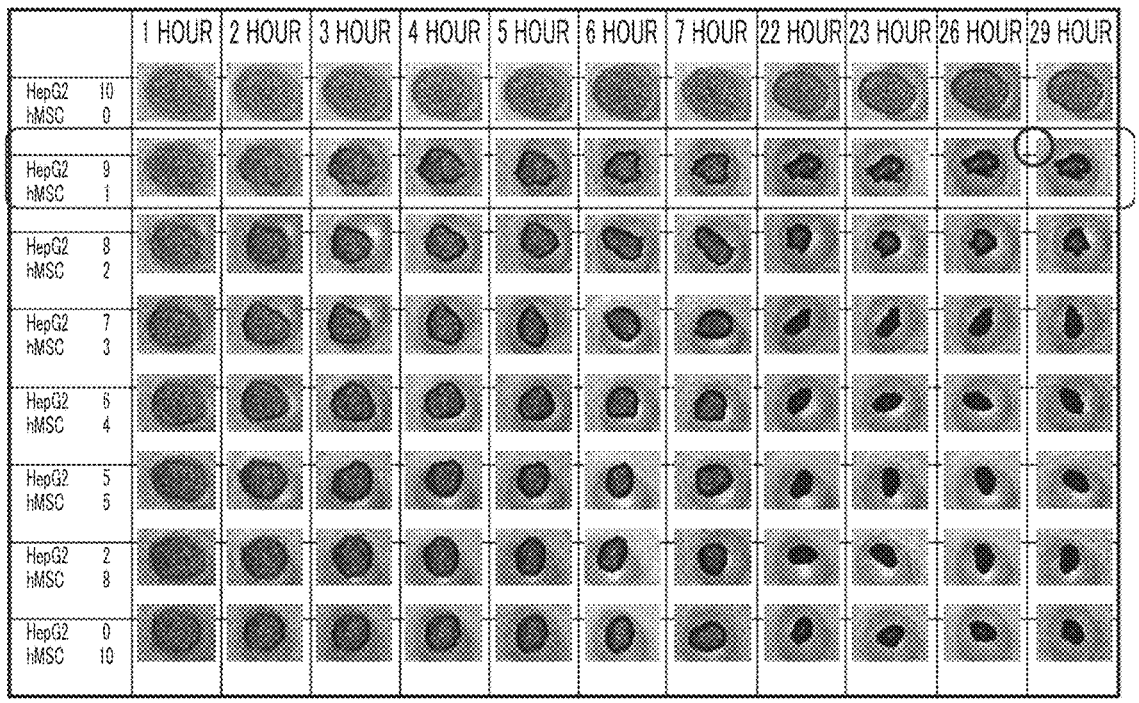
FIG. 4 shows a formation of a mosaic cell aggregation of a HepG2 cell (human liver cancer-derived cell) and hMSC (human bone marrow-derived mesenchymal stem cell).
Figure 5:
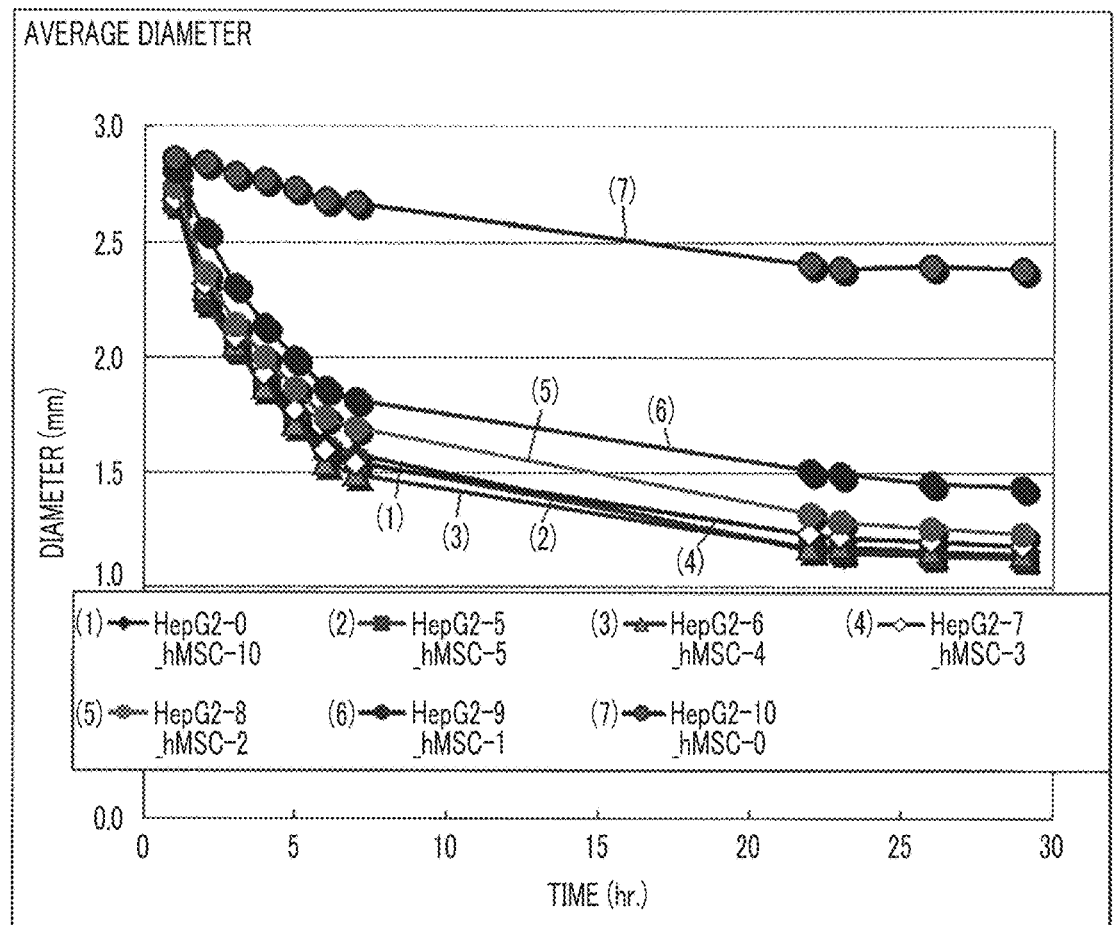
FIG. 5 shows a formation of a mosaic cell aggregation of a HepG2 cell (human liver cancer-derived cell) and hMSC (human bone marrow-derived mesenchymal stem cell).

In a case where a mosaic cell aggregation was formed using a HepG2 cell (human liver cancer-derived cell) as a first cell and hMSC (human bone marrow-derived mesenchymal stem cell) as a second cell, acceleration of the formation of the mosaic cell aggregation was observed in FIGS. 4 and 5 by mixing 10% of hMSC with the HepG2 cell, compared to a case where the mosaic cell aggregation was formed of only the HepG2 cell (100%). In addition, the formation of the mosaic cell aggregation is further accelerated by increasing the proportion of the number of hMSC cells to 20% and 30%. On the other hand, even in a case where the proportion of the number of hMSC cells are increased to about 40% and 50%, there was no significant acceleration of the formation of the mosaic cell aggregation compared to the case where the above-described proportion is 30%. Therefore, in the combination of these cells, it was found that sufficient acceleration is obtained through the addition of about 30% of hMSC.

Figure 6:
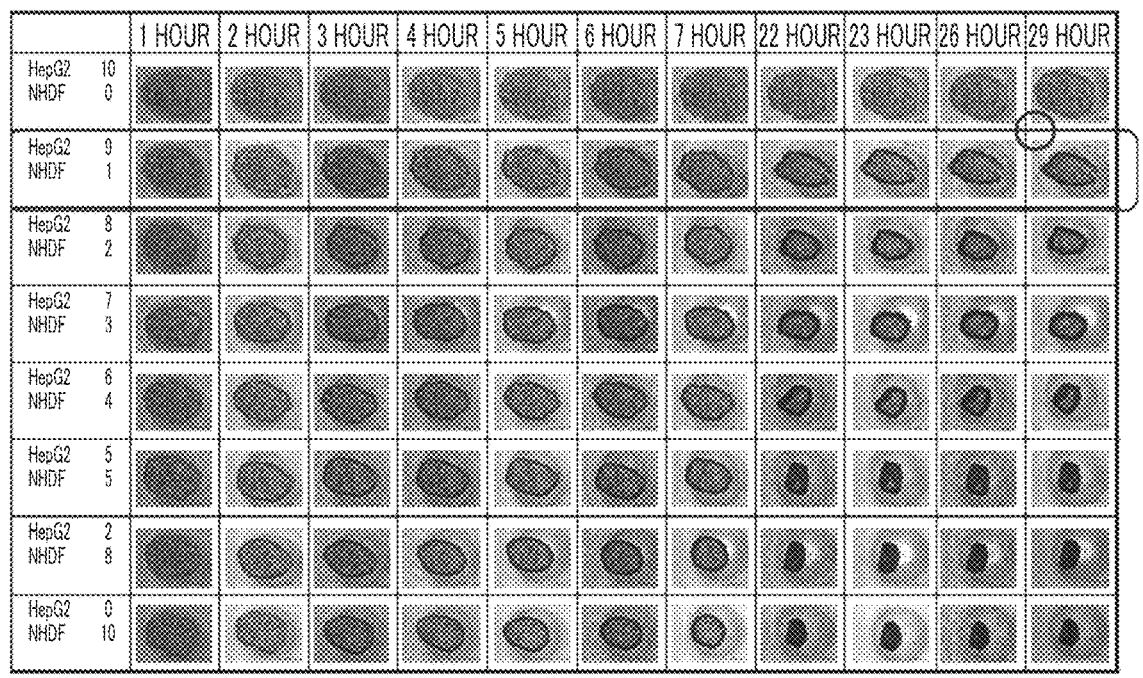
FIG. 6 shows a formation of a mosaic cell aggregation of a HepG2 cell (human liver cancer-derived cell) and NHDF (normal human skin fibroblast).
Figure 7:
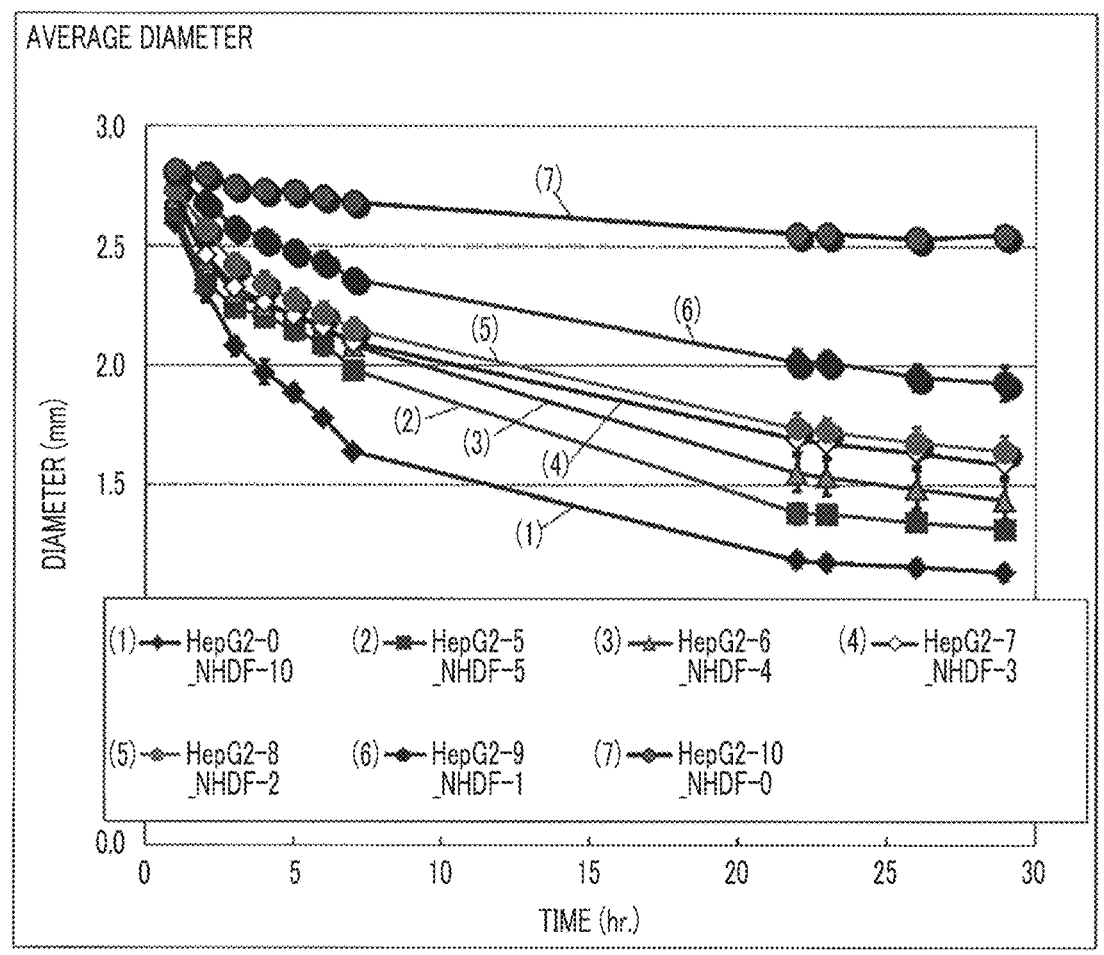
FIG. 7 shows a formation of a mosaic cell aggregation of a HepG2 cell (human liver cancer-derived cell) and NHDF (normal human skin fibroblast).

In a case where a mosaic cell aggregation was formed using a HepG2 cell as a first cell and NHDF (normal human skin fibroblast) as a second cell, acceleration of the formation of the mosaic cell aggregation was observed in FIGS. 6 and 7 by mixing 10% of NHDF with the HepG2 cell, compared to a case where the mosaic cell aggregation was formed of only the HepG2 cell (100%). In addition, it was found that the formation of the mosaic cell aggregation is further accelerated by increasing the proportion of the number of NHDF cells to 10%, 20%, 30%, 40%, and 50%. In the combination of these cells, it was found that the formation of the mosaic cell aggregation is accelerated as NHDF is added.

Figure 8:
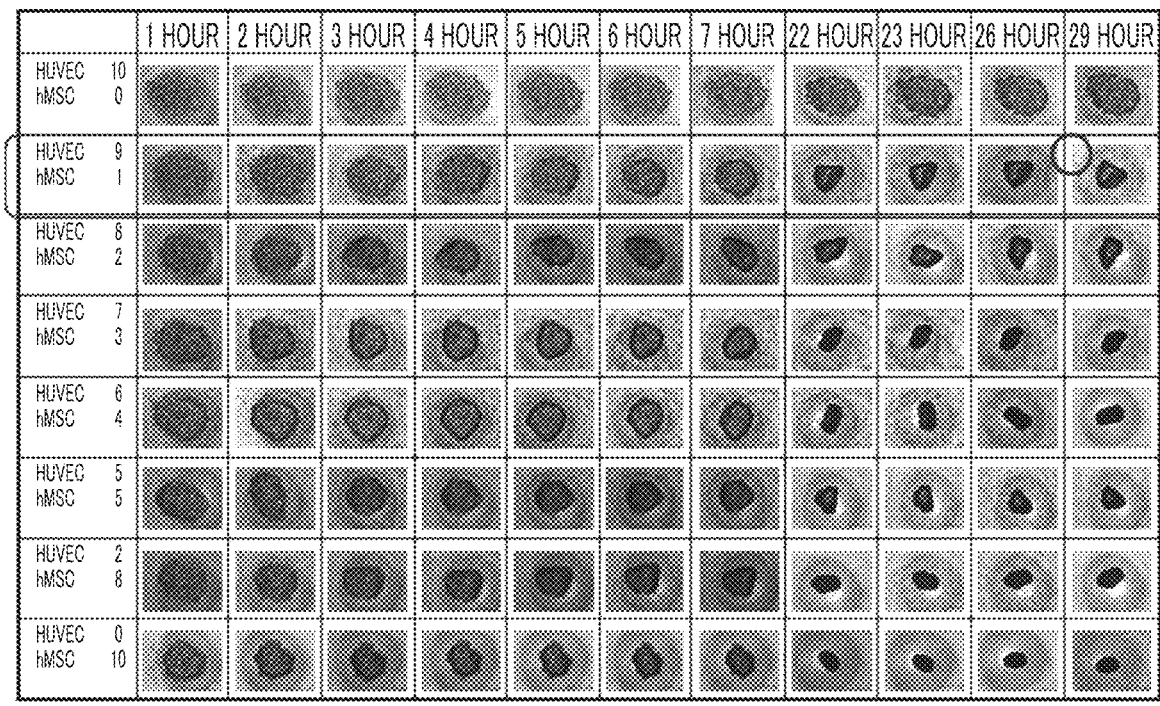
FIG. 8 shows a formation of a mosaic cell aggregation of a HUVEC cell (human umbilical vein endothelial cell) and hMSC (human bone marrow-derived mesenchymal stem cell).
Figure 9:
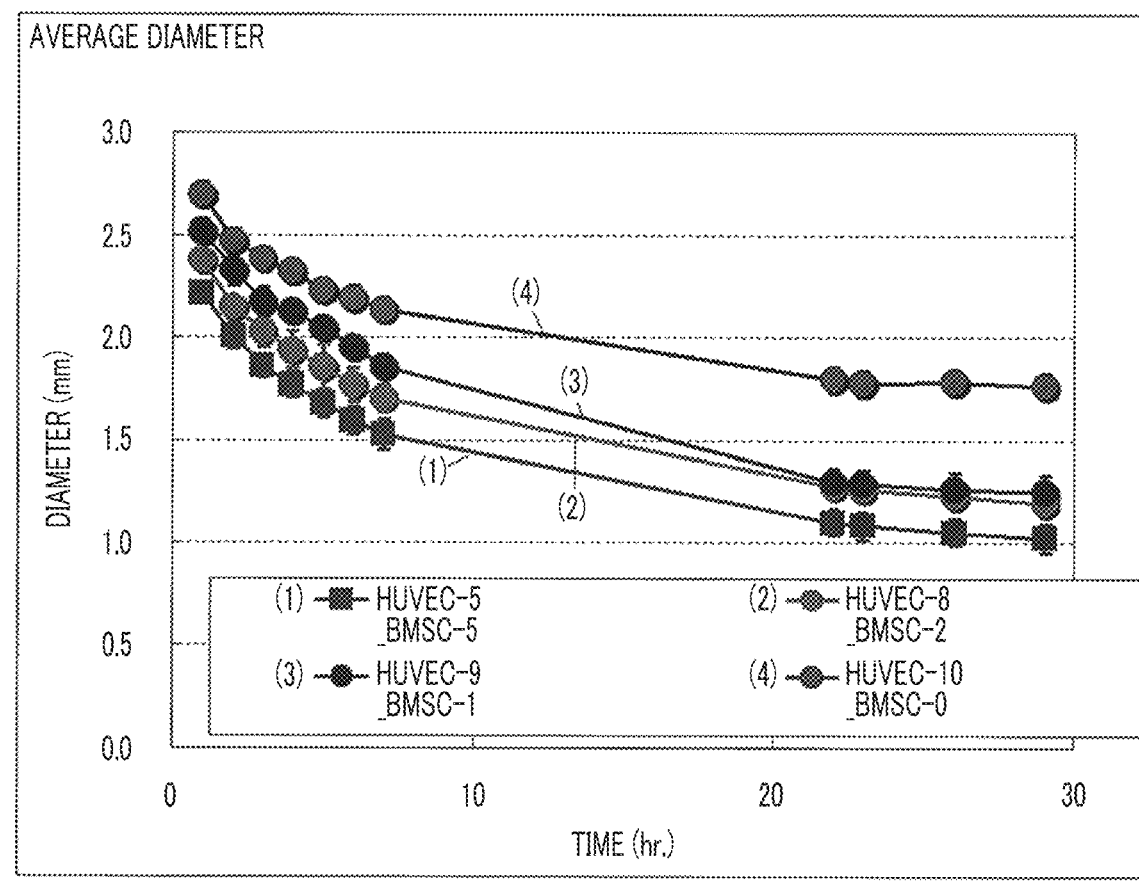
FIG. 9 shows a formation of a mosaic cell aggregation of a HUVEC cell (human umbilical vein endothelial cell) and hMSC (human bone marrow-derived mesenchymal stem cell).

In a case where a mosaic cell aggregation was formed using a HUVEC cell (human umbilical vein endothelial cell) as a first cell and hMSC (human bone marrow-derived mesenchymal stem cell) as a second cell, acceleration of the formation of the mosaic cell aggregation was observed in FIGS. 8 and 9 by mixing 10% of hMSC with the HUVEC cell, compared to a case where the mosaic cell aggregation was formed of only the HUVEC cell (100%).

Figure 10:
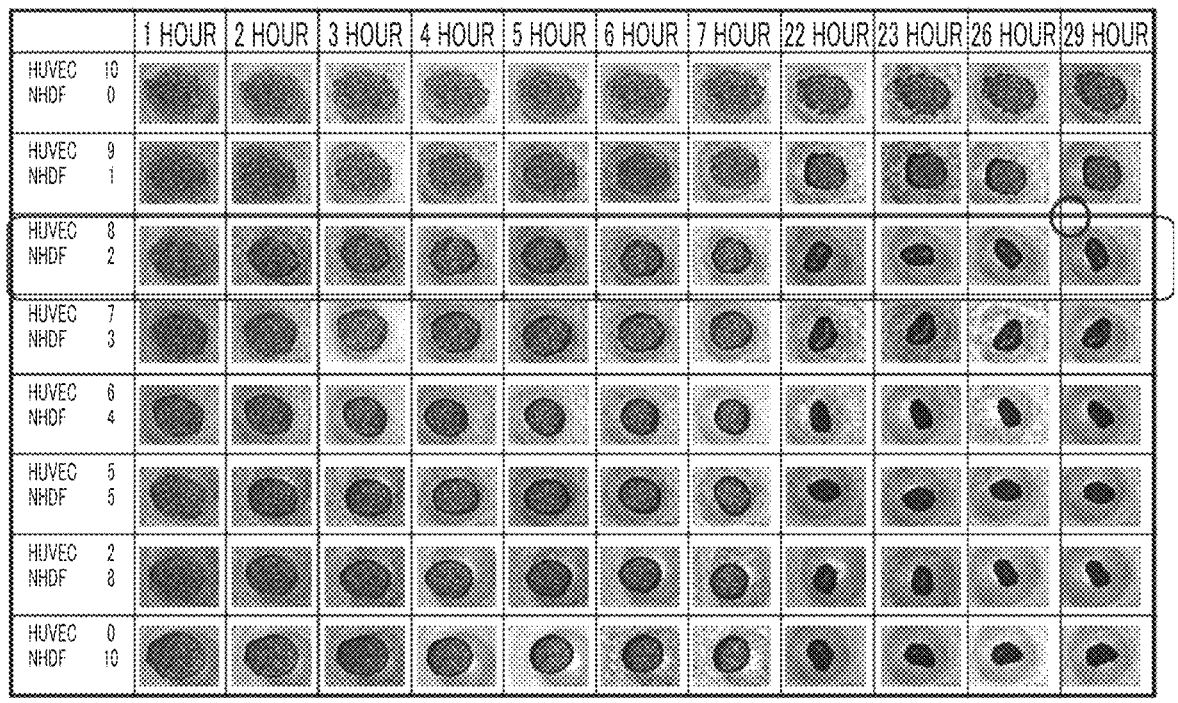
FIG. 10 shows a formation of a mosaic cell aggregation of a HUVEC cell (human umbilical vein endothelial cell) and NHDF (normal human skin fibroblast).
Figure 11:
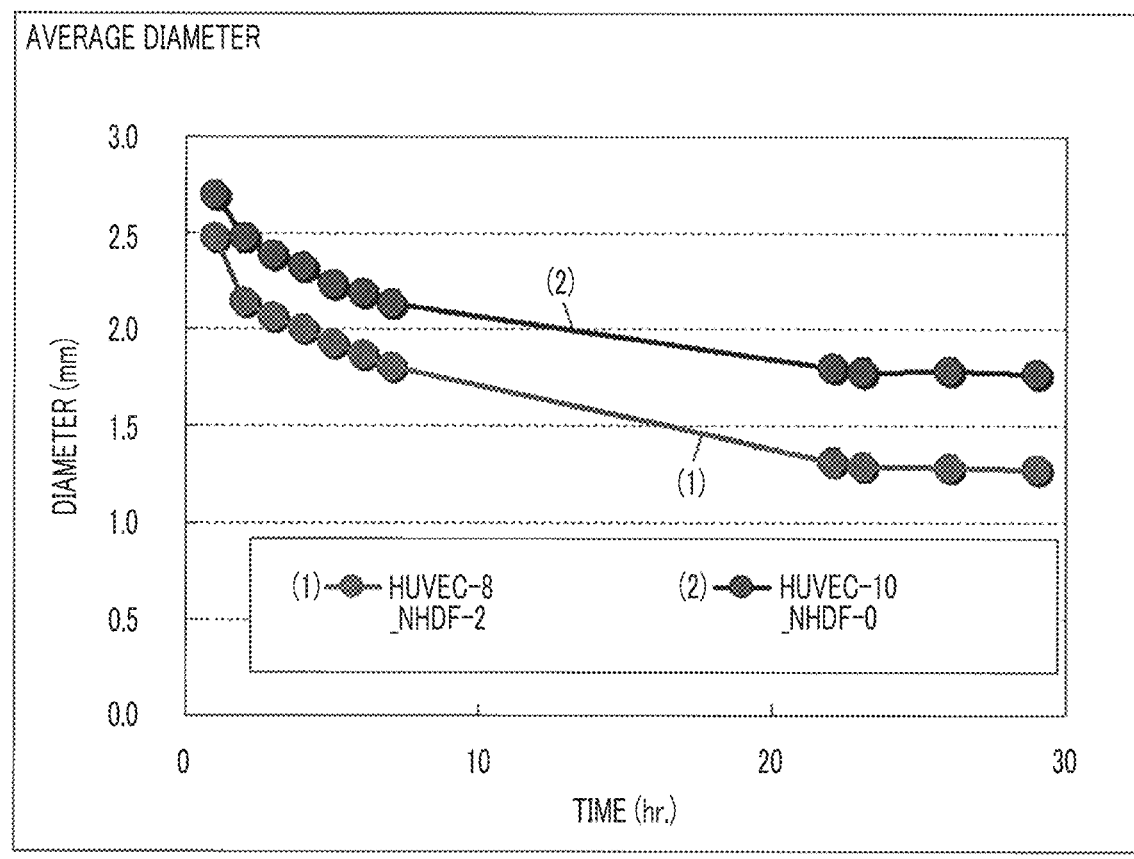
FIG. 11 shows a formation of a mosaic cell aggregation of a HUVEC cell (human umbilical vein endothelial cell) and NHDF (normal human skin fibroblast).

In a case where a mosaic cell aggregation was formed using a HUVEC cell as a first cell and NHDF (normal human skin fibroblast) as a second cell, acceleration of the formation of the mosaic cell aggregation was observed in FIGS. 10 and 11 by mixing 10% or greater than or equal to 20% of NHDF with the HUVEC cell, compared to a case where the mosaic cell aggregation was formed of only the HUVEC cell (100%).

In a case where a mosaic cell aggregation was formed using a HUVEC cell as a first cell and BdSMC (normal human bladder smooth muscle cell) as a second cell, acceleration of the formation of the mosaic cell aggregation was observed in FIG. 12 by mixing 20% of BdSMC with the HUVEC cell, compared to a case where the mosaic cell aggregation was formed of only the HUVEC cell (100%).

As described above, it became clear that the formation of a mosaic cell aggregation in a state of containing a macromolecular block can be unexpectedly accelerated by adding a certain kind of cell to a cell which slowly forms a mosaic cell aggregation in a case of being used alone.

TABLE 1

| First cell | Second cell | First cell:Second cell (proportion of number of cells) | | | | | | | |
|---|---|---|---|---|---|---|---|---|---|
| HepG2 | hMSC | 10:0 | 9:1 | 8:2 | 7:3 | 6:4 | 5:5 | 2:8 | 0:10 |
| HepG2 | NHDF | 10:0 | 9:1 | 8:2 | 7:3 | 6:4 | 5:5 | 2:8 | 0:10 |

TABLE 1-continued

| First cell | Second cell | First cell:Second cell (proportion of number of cells) | | | | | | | |
|---|---|---|---|---|---|---|---|---|---|
| HUVEC | hMSC | 10:0 | 9:1 | 8:2 | 7:3 | 6:4 | 5:5 | 2:8 | 0:10 |
| HUVEC | NHDF | 10:0 | 9:1 | 8:2 | 7:3 | 6:4 | 5:5 | 2:8 | 0:10 |
| HUVEC | BdSMC | 10:0 | | 8:2 | | | | | |

SEQUENCE TABLE

International Application 16F00478 Cell Structure and Production of Cell Structure JP16070211 20160708----00130388051601428687 Normal 20160708094731201606211624522780_P1AP101_16_1.app Based on International Patent Cooperation Treaty

What is claimed is:

1. A method for producing a cell structure comprising a biocompatible macromolecular block; and two or more kinds of cells,
   wherein a plurality of the biocompatible macromolecular blocks are arranged in gaps between a plurality of the cells,
   wherein the two or more kinds of cells contain at least one kind of first cell selected from the group consisting of vascular endothelial cells, and liver cells, and at least one kind of second cell selected from the group consisting of fibroblasts, smooth muscle cells, and mesenchymal stem cells, and
   wherein the ratio of the number of cells of the first cell to the second cell is 9:1 to 2:8,
   the method comprising incubating a mixture of a biocompatible macromolecular block and a culture solution containing two or more kinds of cells.

2. The method for producing a cell structure according to claim 1,
   wherein a size of the biocompatible macromolecular block is 10 μm to 300 μm.

3. The method for producing a cell structure according to claim 1,
   wherein a thickness or a diameter of the cell structure is 400 μm to 3 μm.

4. The method for producing a cell structure according to claim 1,
   wherein a tap density of the biocompatible macromolecular block is 10 mg/cm$^3$ to 500 mg/cm$^3$.

5. The method for producing a cell structure according to claim 1,
   wherein a biocompatible macromolecule is cross-linked in the biocompatible macromolecular block.

6. The method for producing a cell structure according to claim 5,
   wherein the cross-linking degree of the biocompatible macromolecular block is greater than or equal to 2, and the water absorption rate of the biocompatible macromolecular block is greater than or equal to 300%.

7. The method for producing a cell structure according to claim 1,
   wherein the biocompatible macromolecular block is obtained by pulverizing a solid matter containing a biocompatible macromolecule.

8. The method for producing a cell structure according to claim 7,
   wherein the solid matter is obtained by freeze-drying an aqueous solution containing a biocompatible macromolecule.

9. The method for producing a cell structure according to claim 1,
   wherein 0.0000001 μg to 1 μg of the biocompatible macromolecular block is contained per cell.

10. The method for producing a cell structure according to claim 1,
    wherein the biocompatible macromolecule is recombinant gelatin.

11. The method for producing a cell structure according to claim 10,
    wherein the recombinant gelatin is represented by the following formula $$A\text{-}[(Gly\text{-}X\text{-}Y)_n]_m\text{-}B \qquad \text{Formula:}$$

(wherein A represents any amino acid or amino acid sequence, B represents any amino acid or amino acid sequence, each X of total n independently represents any amino acid, each Y of total n independently represents any amino acid, n represents an integer of 3 to 100, m represents an integer of 2 to 10, and each Gly-X-Y of total n may be the same as or different from each other.

12. The method for producing a cell structure according to claim 10,
    wherein the recombinant gelatin is any one of
    a peptide formed of an amino acid sequence described in SEQ ID No: 1;
    a peptide which is formed of an amino acid sequence in which one or several amino acids are deleted, substituted, or added in the amino acid sequence described in SEQ ID No: 1, and has biocompatibility; and
    a peptide which is formed of an amino acid sequence having 80% or more sequence identity to the amino acid sequence described in SEQ ID No: 1, and has biocompatibility.

* * * * *

```
SEQUENCE LISTING

<160> NUMBER OF SEQ ID NOS: 11

<210> SEQ ID NO 1
<211> LENGTH: 571
<212> TYPE: PRT
<213> ORGANISM: Artificial Sequence
<220> FEATURE:
<223> OTHER INFORMATION: Synthetic recombinant peptide sequence

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Pro
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
    210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255
```

```
Glu Arg Gly Asp Ala Gly Pro Lys Gly Ala Asp Gly Ala Pro Gly Lys
            260                 265                 270

Asp Gly Val Arg Gly Leu Ala Gly Pro Ile Gly Pro Pro Gly Glu Arg
            275                 280                 285

Gly Ala Ala Gly Leu Pro Gly Pro Lys Gly Glu Arg Gly Asp Ala Gly
            290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Pro Ala Gly Ala Pro Gly Ala Pro
                325                 330                 335

Gly Leu Gln Gly Met Pro Gly Glu Arg Gly Ala Ala Gly Leu Pro Gly
            340                 345                 350

Pro Lys Gly Glu Arg Gly Asp Ala Gly Pro Lys Gly Ala Asp Gly Ala
            355                 360                 365

Pro Gly Lys Asp Gly Val Arg Gly Leu Ala Gly Pro Pro Gly Ala Pro
            370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Glu Arg Gly Asp Ala Gly Pro
                405                 410                 415

Lys Gly Ala Asp Gly Ala Pro Gly Ala Pro Gly Leu Gln Gly Met Pro
            420                 425                 430

Gly Glu Arg Gly Ala Ala Gly Leu Pro Gly Pro Lys Gly Glu Arg Gly
            435                 440                 445

Asp Ala Gly Pro Lys Gly Ala Asp Gly Ala Pro Gly Lys Asp Gly Val
            450                 455                 460

Arg Gly Leu Ala Gly Pro Ile Gly Pro Pro Gly Glu Arg Gly Ala Ala
465                 470                 475                 480

Gly Leu Pro Gly Pro Lys Gly Glu Arg Gly Asp Ala Gly Pro Lys Gly
                485                 490                 495

Ala Asp Gly Ala Pro Gly Lys Asp Gly Val Arg Gly Leu Ala Gly Pro
            500                 505                 510

Ile Gly Pro Pro Gly Pro Ala Gly Ala Pro Gly Ala Pro Gly Leu Gln
            515                 520                 525

Gly Met Pro Gly Glu Arg Gly Ala Ala Gly Leu Pro Gly Pro Lys Gly
            530                 535                 540

Glu Arg Gly Asp Ala Gly Pro Lys Gly Ala Asp Gly Ala Pro Gly Lys
545                 550                 555                 560

Asp Gly Val Arg Gly Leu Ala Gly Pro Pro Gly
            565                 570

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 2

Arg Glu Asp Val
1

<210> SEQ ID NO 3
<211> LENGTH: 5
<212> TYPE: PRT
```

```
<213> ORGANISM: Artificial Sequence
<220> FEATURE:
<223> OTHER INFORMATION: Description of Artificial Sequence: synthetic
      adhesive sequence

<400> SEQUENCE: 3

Tyr Ile Gly Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 4

Pro Asp Ser Gly Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 5

Arg Tyr Val Val Leu Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 6

Leu Gly Thr Ile Pro Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 7

Arg Asn Ile Ala Glu Ile Ile Lys Asp Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 8

Ile Lys Val Ala Val
1               5
```

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 9

Asp Gly Glu Ala
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: synthetic
      adhesive sequence

<400> SEQUENCE: 10

Glu Arg Gly Asp
1

<210> SEQ ID NO 11
<211> LENGTH: 571
<212> TYPE: PRT
<213> ORGANISM: Artificial Sequence
<220> FEATURE:
<223> OTHER INFORMATION: synthetic recombinant gelatin sequence
<220> FEATURE:
<221> NAME/KEY: MISC_FEATURE
<222> LOCATION: (1)..(571)
<223> OTHER INFORMATION: all Xaa is independently any amino acid

<400> SEQUENCE: 11

Gly Ala Pro Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa Gly Xaa
            20                  25                  30

Xaa Gly Xaa Xaa Gly Xaa Xaa Gly Xaa Xaa Gly Xaa Xaa Gly Xaa Xaa
        35                  40                  45

Gly Xaa Xaa Gly Xaa Xaa Gly Xaa Xaa Gly Xaa Xaa Gly Xaa Xaa Gly
    50                  55                  60

Xaa Xaa Gly Xaa Xaa Gly Xaa Xaa Gly Xaa Xaa Gly Xaa Xaa Gly Xaa
65                  70                  75                  80

Xaa Gly Xaa Xaa Gly Xaa Xaa Gly Xaa Xaa Gly Xaa Xaa Gly Xaa Xaa
                85                  90                  95

Gly Xaa Xaa Gly Xaa Xaa Gly Xaa Xaa Gly Xaa Xaa Gly Xaa Xaa Gly
            100                 105                 110

Xaa Xaa Gly Xaa Xaa Gly Xaa Xaa Gly Xaa Xaa Gly Xaa Xaa Gly Xaa
        115                 120                 125

Xaa Gly Xaa Xaa Gly Xaa Xaa Gly Xaa Xaa Gly Xaa Xaa Gly Xaa Xaa
    130                 135                 140

Gly Xaa Xaa Gly Xaa Xaa Gly Xaa Xaa Gly Xaa Xaa Gly Xaa Xaa Gly
145                 150                 155                 160

Xaa Xaa Gly Xaa Xaa Gly Xaa Xaa Gly Xaa Xaa Gly Xaa Xaa Gly Xaa
                165                 170                 175

Xaa Gly Xaa Xaa Gly Xaa Xaa Gly Xaa Xaa Gly Xaa Xaa Gly Xaa Xaa
            180                 185                 190

Gly Xaa Xaa Gly Xaa Xaa Gly Xaa Xaa Gly Xaa Xaa Gly
        195                 200                 205

Xaa Xaa Gly Xaa Xaa Gly Xaa Xaa Gly Xaa Xaa Gly Xaa
    210                 215                 220

Xaa Gly Xaa Xaa Gly Xaa Xaa Gly Xaa Xaa Gly Xaa Xaa
225                 230                 235                 240

Gly Xaa Xaa Gly Xaa Xaa Gly Xaa Xaa Gly Xaa Xaa Gly
            245                 250                 255

Xaa Xaa Gly Xaa Xaa Gly Xaa Xaa Gly Xaa Xaa Gly Xaa
        260                 265                 270

Xaa Gly Xaa Xaa Gly Xaa Xaa Gly Xaa Xaa Gly Xaa Xaa
    275                 280                 285

Gly Xaa Xaa Gly Xaa Xaa Gly Xaa Xaa Gly Xaa Xaa Gly
290                 295                 300

Xaa Xaa Gly Xaa Xaa Gly Xaa Xaa Gly Xaa Xaa Gly Xaa
305                 310                 315                 320

Xaa Gly Xaa Xaa Gly Xaa Xaa Gly Xaa Xaa Gly Xaa Xaa
            325                 330                 335

Gly Xaa Xaa Gly Xaa Xaa Gly Xaa Xaa Gly Xaa Xaa Gly
        340                 345                 350

Xaa Xaa Gly Xaa Xaa Gly Xaa Xaa Gly Xaa Xaa Gly Xaa
    355                 360                 365

Xaa Gly Xaa Xaa Gly Xaa Xaa Gly Xaa Xaa Gly Xaa Xaa
370                 375                 380

Gly Xaa Xaa Gly Xaa Xaa Gly Xaa Xaa Gly Xaa Xaa Gly
385                 390                 395                 400

Xaa Xaa Gly Xaa Xaa Gly Xaa Xaa Gly Xaa Xaa Gly Xaa
            405                 410                 415

Xaa Gly Xaa Xaa Gly Xaa Xaa Gly Xaa Xaa Gly Xaa Xaa
        420                 425                 430

Gly Xaa Xaa Gly Xaa Xaa Gly Xaa Xaa Gly Xaa Xaa Gly
    435                 440                 445

Xaa Xaa Gly Xaa Xaa Gly Xaa Xaa Gly Xaa Xaa Gly Xaa
    450                 455                 460

Xaa Gly Xaa Xaa Gly Xaa Xaa Gly Xaa Xaa Gly Xaa Xaa
465                 470                 475                 480

Gly Xaa Xaa Gly Xaa Xaa Gly Xaa Xaa Gly Xaa Xaa Gly
            485                 490                 495

Xaa Xaa Gly Xaa Xaa Gly Xaa Xaa Gly Xaa Xaa Gly Xaa
        500                 505                 510

Xaa Gly Xaa Xaa Gly Xaa Xaa Gly Xaa Xaa Gly Xaa Xaa
    515                 520                 525

Gly Xaa Xaa Gly Xaa Xaa Gly Xaa Xaa Gly Xaa Xaa Gly
530                 535                 540

Xaa Xaa Gly Xaa Xaa Gly Xaa Xaa Gly Xaa Xaa Gly Xaa
545                 550                 555                 560

Xaa Gly Xaa Xaa Gly Xaa Xaa Gly Xaa Xaa Gly
            565                 570